(12) United States Patent
Foster et al.

(10) Patent No.: US 11,510,697 B2
(45) Date of Patent: Nov. 29, 2022

(54) TOOLS AND SYSTEMS FOR IMPLANTING AND/OR RETRIEVING A LEADLESS CARDIAC PACING DEVICE WITH HELIX FIXATION

(71) Applicant: CARDIAC PACEMAKERS, INC., St. Paul, MN (US)

(72) Inventors: Arthur J. Foster, Blaine, MN (US); Dana Sachs, Pine City, MN (US); Brendan Early Koop, Ham Lake, MN (US); Justin Robert Alt, Minneapolis, MN (US); David Robert Wulfman, Minneapolis, MN (US); Benjamin J. Haasl, Forest Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 182 days.

(21) Appl. No.: 17/016,936

(22) Filed: Sep. 10, 2020

(65) Prior Publication Data

US 2021/0068868 A1 Mar. 11, 2021

Related U.S. Application Data

(60) Provisional application No. 62/898,701, filed on Sep. 11, 2019.

(51) Int. Cl.
*A61N 1/37* (2006.01)
*A61B 17/34* (2006.01)
(Continued)

(52) U.S. Cl.
CPC .......... *A61B 17/3468* (2013.01); *A61N 1/056* (2013.01); *A61N 1/3756* (2013.01);
(Continued)

(58) Field of Classification Search
CPC ...... A61B 17/3456; A61B 2017/00292; A61B 2017/00358; A61N 1/3756
See application file for complete search history.

(56) References Cited

U.S. PATENT DOCUMENTS 4,301,815 A 11/1981 Doring
4,582,056 A * 4/1986 McCorkle, Jr. ........ A61B 17/29
606/1

(Continued)

FOREIGN PATENT DOCUMENTS

EP 1453414 A2 9/2004
EP 2769750 A1 8/2014
(Continued)

OTHER PUBLICATIONS

International Search Report and Written Opinion dated Mar. 8, 2019 for International Application No. PCT/US2018/066422.
(Continued)

*Primary Examiner* — Eric D. Bertram
(74) *Attorney, Agent, or Firm* — Seager, Tufte & Wickhem LLP

(57) ABSTRACT

An implantation and/or retrieval device for a leadless cardiac pacing device may include a first elongate shaft including a lumen; a second elongate shaft slidably disposed within the lumen of the first elongate shaft; an end cap assembly fixedly attached to a distal end of the first elongate shaft; and a plurality of wires attached to the second elongate shaft and extending distally from the end cap assembly, the plurality of wires being movable relative to the end cap assembly. The plurality of wires is configured to engage a proximal hub of the leadless cardiac pacing device. The plurality of wires forms a plurality of wire loops extending distally from the end cap assembly.

20 Claims, 24 Drawing Sheets

(51) Int. Cl.
  *A61N 1/375* (2006.01)
  *A61N 1/05* (2006.01)
  *A61B 17/00* (2006.01)
  *A61N 1/362* (2006.01)

(52) U.S. Cl.
  CPC .... *A61N 1/37512* (2017.08); *A61B 2017/00292* (2013.01); *A61B 2017/00358* (2013.01); *A61B 2017/00477* (2013.01); *A61N 1/362* (2013.01); *A61N 2001/058* (2013.01)

(56) References Cited

U.S. PATENT DOCUMENTS

| | | |
|---|---|---|
| 5,147,379 A | 9/1992 | Sabbaghian et al. |
| 5,170,802 A | 12/1992 | Mehra |
| 5,238,004 A | 8/1993 | Sahatjian et al. |
| 5,540,236 A | 7/1996 | Ginn |
| 5,803,928 A | 9/1998 | Tockman et al. |
| 5,807,399 A | 9/1998 | Laske et al. |
| 5,908,381 A | 6/1999 | Aznoian et al. |
| 5,925,073 A | 7/1999 | Chastain et al. |
| 5,957,842 A | 9/1999 | Littmann et al. |
| 6,070,104 A | 5/2000 | Hine et al. |
| 6,164,284 A | 12/2000 | Schulman et al. |
| 6,181,973 B1 | 1/2001 | Ceron et al. |
| 6,185,452 B1 | 2/2001 | Schulman et al. |
| 6,224,725 B1 | 5/2001 | Glocker |
| 6,231,516 B1 | 5/2001 | Keilman et al. |
| 6,395,017 B1 | 5/2002 | Dwyer et al. |
| 6,409,101 B1 | 6/2002 | D'Arrigo |
| 6,409,674 B1 | 6/2002 | Brockway et al. |
| 6,416,474 B1 | 7/2002 | Penner et al. |
| 6,442,413 B1 | 8/2002 | Silver |
| 6,445,953 B1 | 9/2002 | Bulkes et al. |
| 6,497,803 B2 | 12/2002 | Glocker et al. |
| 6,508,803 B1 | 1/2003 | Horikawa et al. |
| 6,551,477 B2 | 4/2003 | Glocker et al. |
| 6,582,441 B1 | 6/2003 | He et al. |
| 6,584,362 B1 | 6/2003 | Scheiner et al. |
| 6,592,518 B2 | 7/2003 | Denker et al. |
| 6,638,268 B2 | 10/2003 | Niazi |
| 6,783,499 B2 | 8/2004 | Schwartz |
| 6,786,918 B1 | 9/2004 | Krivoruchko et al. |
| 6,907,285 B2 | 6/2005 | Denker et al. |
| 7,003,350 B2 | 2/2006 | Denker et al. |
| 7,082,336 B2 | 7/2006 | Ransbury et al. |
| 7,114,502 B2 | 10/2006 | Schulman et al. |
| 7,164,852 B2 | 1/2007 | Cazzini et al. |
| 7,212,870 B1 | 5/2007 | Helland |
| 7,236,821 B2 | 6/2007 | Cates et al. |
| 7,248,913 B2 | 7/2007 | Hassett |
| 7,295,879 B2 | 11/2007 | Denker et al. |
| 7,309,354 B2 | 12/2007 | Mathis et al. |
| 7,310,556 B2 | 12/2007 | Bulkes |
| 7,313,444 B2 | 12/2007 | Pianca et al. |
| 7,321,798 B2 | 1/2008 | Muhlenberg et al. |
| 7,381,216 B2 | 6/2008 | Buzzard et al. |
| 7,425,200 B2 | 9/2008 | Brockway et al. |
| 7,499,758 B2 | 3/2009 | Cates et al. |
| 7,509,169 B2 | 3/2009 | Eigler et al. |
| 7,519,421 B2 | 4/2009 | Denker et al. |
| 7,529,589 B2 | 5/2009 | Williams et al. |
| 7,535,296 B2 | 5/2009 | Bulkes et al. |
| 7,572,228 B2 | 8/2009 | Wolinsky et al. |
| 7,608,099 B2 | 10/2009 | Johnson et al. |
| 7,617,007 B2 | 11/2009 | Williams et al. |
| 7,666,203 B2 | 2/2010 | Chanduszko et al. |
| 7,678,081 B2 | 3/2010 | Whiting et al. |
| 7,711,434 B2 | 5/2010 | Denker et al. |
| 7,734,343 B2 | 6/2010 | Ransbury et al. |
| 7,747,335 B2 | 6/2010 | Williams |
| 7,749,265 B2 | 7/2010 | Denker et al. |
| 7,769,466 B2 | 8/2010 | Denker et al. |
| 7,799,037 B1 | 9/2010 | He et al. |
| 7,801,626 B2 | 9/2010 | Moser |
| 7,826,903 B2 | 11/2010 | Denker et al. |
| 7,840,281 B2 | 11/2010 | Kveen et al. |
| 7,840,282 B2 | 11/2010 | Williams et al. |
| 7,865,249 B2 | 1/2011 | Reddy |
| 7,894,915 B1 | 2/2011 | Chitre et al. |
| 7,899,554 B2 | 3/2011 | Williams et al. |
| 7,937,148 B2 | 5/2011 | Jacobson |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 3,032,219 A1 | 10/2011 | Neumann et al. |
| 8,050,775 B2 | 11/2011 | Westlund et al. |
| 8,103,359 B2 | 1/2012 | Reddy |
| 8,103,361 B2 | 1/2012 | Moser |
| 8,116,883 B2 | 2/2012 | Williams et al. |
| 8,160,722 B2 | 4/2012 | Rutten et al. |
| 8,185,213 B2 | 5/2012 | Kveen et al. |
| 8,204,596 B2 | 6/2012 | Ransbury et al. |
| 8,224,463 B2 | 7/2012 | Worley |
| 8,239,045 B2 | 8/2012 | Ransbury et al. |
| 8,244,376 B2 | 8/2012 | Worley |
| 8,267,987 B2 | 9/2012 | Johnson et al. |
| 8,308,794 B2 | 11/2012 | Martinson et al. |
| 8,311,633 B2 | 11/2012 | Ransbury et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,489,189 B2 | 7/2013 | Tronnes |
| 8,489,205 B2 | 7/2013 | Stotts et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,571,678 B2 | 10/2013 | Wang |
| 8,615,310 B2 | 12/2013 | Khairkhahan et al. |
| 8,626,299 B2 | 1/2014 | Gross et al. |
| 8,630,710 B2 | 1/2014 | Kumar et al. |
| 8,634,280 B1 | 1/2014 | Wang et al. |
| 8,634,912 B2 | 1/2014 | Bornzin et al. |
| 8,634,919 B1 | 1/2014 | Hou et al. |
| 8,644,934 B2 | 2/2014 | Hastings et al. |
| 8,670,824 B2 | 3/2014 | Andersen et al. |
| 8,670,842 B1 | 3/2014 | Bornzin et al. |
| 8,676,349 B2 | 3/2014 | Stalker et al. |
| 8,700,181 B2 | 4/2014 | Bornzin et al. |
| 8,712,553 B2 | 4/2014 | Reddy |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,781,605 B2 | 7/2014 | Bornzin et al. |
| 8,798,740 B2 | 8/2014 | Samade et al. |
| 8,798,770 B2 | 8/2014 | Reddy |
| 8,855,789 B2 | 10/2014 | Jacobson |
| 8,886,340 B2 | 11/2014 | Williams et al. |
| 8,894,824 B2 | 11/2014 | Glocker et al. |
| 8,903,513 B2 | 12/2014 | Ollivier |
| 8,903,573 B2 | 12/2014 | Chandra et al. |
| 8,914,131 B2 | 12/2014 | Bornzin et al. |
| 8,926,588 B2 | 1/2015 | Berthiaume et al. |
| 8,938,294 B2 | 1/2015 | Anderson et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 8,989,873 B2 | 3/2015 | Locsin |
| 8,992,545 B2 | 3/2015 | Cahill |
| 8,996,109 B2 | 3/2015 | Karst et al. |
| 9,008,777 B2 | 4/2015 | Dianaty et al. |
| 9,017,341 B2 | 4/2015 | Bornzin et al. |
| 9,020,611 B2 | 4/2015 | Khairkhahan et al. |
| 9,026,229 B2 | 5/2015 | Stalker et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |

(56) References Cited

U.S. PATENT DOCUMENTS

| Patent/Publication No. | Date | Inventor(s) |
|---|---|---|
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,289,612 B1 | 3/2016 | Sambelashvili et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,339,646 B2 | 5/2016 | Ollivier |
| 9,351,648 B2 | 5/2016 | Mothilal et al. |
| 9,358,387 B2 | 6/2016 | Suwito et al. |
| 9,393,427 B2 | 7/2016 | Schmidt et al. |
| 9,399,140 B2 | 7/2016 | Cho et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,755 B2 | 10/2016 | Westlund et al. |
| 9,468,773 B1 | 10/2016 | Anderson et al. |
| 9,480,850 B2 | 11/2016 | Schmidt et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,533,163 B2 | 1/2017 | Klimovitch et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,669,223 B2 | 6/2017 | Auricchio et al. |
| 9,675,798 B2 | 6/2017 | Grubac et al. |
| 9,713,427 B2 | 7/2017 | Stalker et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,827,426 B2 | 11/2017 | Reddy |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 9,878,151 B2 | 1/2018 | Bornzin et al. |
| 9,889,295 B2 | 2/2018 | Ollivier |
| 9,956,400 B2 | 5/2018 | Haasl et al. |
| 9,974,948 B2 | 5/2018 | Ollivier |
| 9,993,648 B2 | 6/2018 | Kelly et al. |
| 10,080,888 B2 | 9/2018 | Kelly et al. |
| 10,124,163 B2 | 11/2018 | Ollivier et al. |
| 10,130,821 B2 | 11/2018 | Grubac et al. |
| 10,159,834 B2 | 12/2018 | Drake et al. |
| 10,188,425 B2 | 1/2019 | Khairkhahan et al. |
| 10,194,927 B2 | 2/2019 | Chu et al. |
| 10,279,168 B2 | 5/2019 | Anderson |
| 10,350,408 B2 | 7/2019 | Wood et al. |
| 10,350,416 B2 | 7/2019 | Bonner et al. |
| 10,390,720 B2 | 8/2019 | Anderson et al. |
| 10,398,901 B2 | 10/2019 | Koop |
| 10,449,354 B2 | 11/2019 | Demmer et al. |
| 10,716,944 B2 | 7/2020 | Haasl et al. |
| 2003/0078618 A1 | 4/2003 | Fey et al. |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2006/0122522 A1 | 6/2006 | Chavan et al. |
| 2006/0241732 A1 | 10/2006 | Denker et al. |
| 2007/0106357 A1 | 5/2007 | Denker et al. |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0029598 A1 | 2/2012 | Zhao |
| 2012/0095539 A1 | 4/2012 | Khairkhahan et al. |
| 2012/0108922 A1 | 5/2012 | Schell et al. |
| 2012/0108986 A1 | 5/2012 | Beasley et al. |
| 2012/0109148 A1 | 5/2012 | Bonner et al. |
| 2012/0165827 A1* | 6/2012 | Khairkhahan ....... A61N 1/3756 606/129 |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197349 A1 | 8/2012 | Griswold et al. |
| 2012/0271134 A1 | 10/2012 | Allan et al. |
| 2012/0323099 A1 | 12/2012 | Mothilal et al. |
| 2013/0012925 A1 | 1/2013 | Berthiaume et al. |
| 2013/0023975 A1 | 1/2013 | Locsin |
| 2013/0035636 A1 | 2/2013 | Beasley et al. |
| 2013/0035748 A1 | 2/2013 | Bonner et al. |
| 2013/0103047 A1 | 4/2013 | Steingisser et al. |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0131591 A1 | 5/2013 | Berthiaume et al. |
| 2013/0138006 A1 | 5/2013 | Bornzin et al. |
| 2013/0192611 A1 | 8/2013 | Taepke, II et al. |
| 2013/0253309 A1 | 9/2013 | Allan et al. |
| 2013/0253342 A1 | 9/2013 | Griswold et al. |
| 2013/0253346 A1 | 9/2013 | Griswold et al. |
| 2013/0253347 A1 | 9/2013 | Griswold et al. |
| 2013/0325081 A1 | 12/2013 | Karst et al. |
| 2013/0345770 A1 | 12/2013 | Dianaty et al. |
| 2014/0018818 A1 | 1/2014 | Somogyi et al. |
| 2014/0058240 A1 | 2/2014 | Mothilal et al. |
| 2014/0100627 A1 | 4/2014 | Min |
| 2014/0107723 A1 | 4/2014 | Hou et al. |
| 2014/0172034 A1 | 6/2014 | Bornzin et al. |
| 2014/0172060 A1 | 6/2014 | Bornzin et al. |
| 2014/0243848 A1 | 8/2014 | Auricchio et al. |
| 2014/0257324 A1 | 9/2014 | Fain |
| 2014/0288576 A1 | 9/2014 | Bornzin et al. |
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |

(56) References Cited

U.S. PATENT DOCUMENTS

| | | |
|---|---|---|
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1* | 3/2016 | Klenk ............... A61N 1/3756 606/129 |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0129239 A1 | 5/2016 | Anderson |
| 2016/0158560 A1 | 6/2016 | Moore et al. |
| 2016/0158561 A1 | 6/2016 | Reddy |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228712 A1 | 8/2016 | Koop |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0252567 A1 | 9/2017 | Koop |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326355 A1 | 11/2017 | Koop et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |
| 2018/0028805 A1 | 2/2018 | Anderson et al. |
| 2018/0030513 A1 | 2/2018 | Hasson |
| 2018/0050191 A1 | 2/2018 | Eby et al. |
| 2018/0050192 A1 | 2/2018 | Nee et al. |
| 2018/0050193 A1 | 2/2018 | Eby et al. |
| 2018/0050194 A1 | 2/2018 | Knippel et al. |
| 2018/0050195 A1 | 2/2018 | Knippel et al. |
| 2018/0071518 A1 | 3/2018 | Drake et al. |
| 2018/0104449 A1 | 4/2018 | Arnar et al. |
| 2018/0104450 A1 | 4/2018 | Rickheim et al. |
| 2018/0104451 A1 | 4/2018 | Kerns et al. |
| 2018/0104452 A1 | 4/2018 | Goodman et al. |
| 2018/0161571 A1 | 6/2018 | Ollivier |
| 2018/0207434 A1 | 7/2018 | Webb et al. |
| 2018/0264256 A1 | 9/2018 | Ollivier |
| 2018/0264262 A1 | 9/2018 | Haasl et al. |
| 2018/0264272 A1 | 9/2018 | Haasl et al. |
| 2018/0264273 A1 | 9/2018 | Hasl et al. |
| 2018/0264274 A1 | 9/2018 | Haasl et al. |
| 2018/0280057 A1 | 10/2018 | Seifert et al. |
| 2018/0280058 A1 | 10/2018 | Meade et al. |
| 2018/0280703 A1 | 10/2018 | Hillukka et al. |
| 2018/0303513 A1 | 10/2018 | Kerns et al. |
| 2018/0303514 A1 | 10/2018 | Coyle et al. |
| 2018/0318590 A1 | 11/2018 | Kabe et al. |
| 2018/0318591 A1 | 11/2018 | Kabe et al. |
| 2018/0339160 A1 | 11/2018 | Carroll |
| 2019/0030346 A1 | 1/2019 | Li et al. |
| 2019/0083800 A1 | 3/2019 | Yang et al. |
| 2019/0126034 A1 | 5/2019 | Drake et al. |
| 2019/0134413 A1 | 5/2019 | Mar et al. |
| 2019/0175219 A1* | 6/2019 | Goodman .......... A61B 17/3468 |
| 2019/0192863 A1 | 6/2019 | Koop et al. |
| 2019/0192864 A1 | 6/2019 | Koop et al. |
| 2019/0351236 A1 | 11/2019 | Koop |
| 2020/0038664 A1 | 3/2020 | Demmer et al. |
| 2020/0306530 A1 | 10/2020 | Koop et al. |
| 2020/0306547 A1 | 10/2020 | Liu et al. |
| 2020/0345396 A1* | 11/2020 | Rickheim ............ A61B 17/50 |

FOREIGN PATENT DOCUMENTS

| | | |
|---|---|---|
| EP | 2818201 B1 | 7/2016 |
| EP | 2658599 B1 | 10/2016 |
| EP | 2651502 B1 | 11/2016 |
| EP | 2771064 B1 | 1/2017 |
| EP | 2780077 B1 | 1/2017 |
| EP | 3056157 B1 | 3/2018 |
| WO | 2008070120 A2 | 6/2008 |
| WO | 2016010958 A1 | 1/2016 |
| WO | 2016011042 A1 | 1/2016 |
| WO | 2016032716 A1 | 3/2016 |
| WO | 2016126465 A1 | 8/2016 |
| WO | 2016172106 A1 | 10/2016 |
| WO | 2019126281 A1 | 6/2019 |

OTHER PUBLICATIONS

International Search Report and Written Opinion dated Mar. 28, 2019 for International Application No. PCT/US2018/066447.

Invite To Pay Additional Fees dated Jun. 15, 2020 for International Application No. PCT/US2020/024842.

International Search Report and Written Opinion dated Jun. 29, 2020 for International Application No. PCT/US2020/0248849.

\* cited by examiner

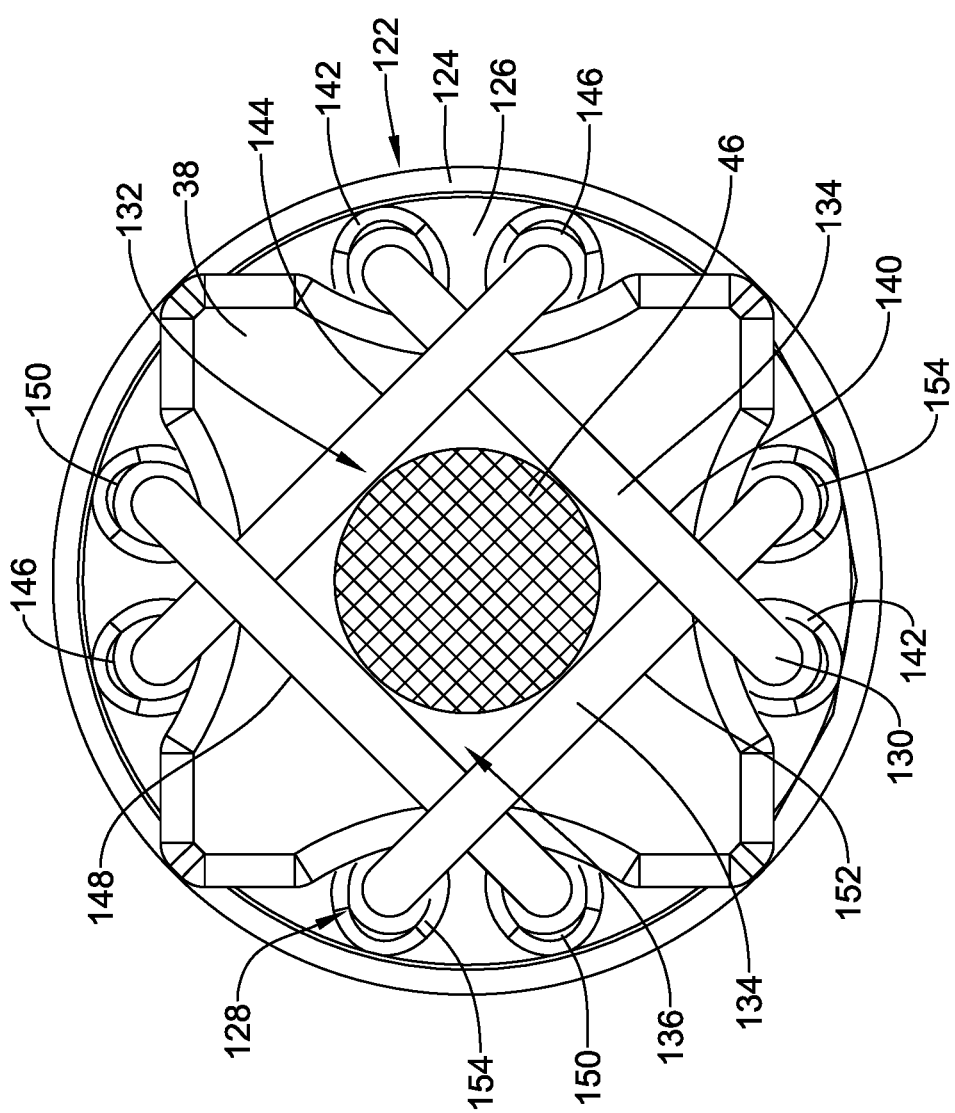

TOOLS AND SYSTEMS FOR IMPLANTING AND/OR RETRIEVING A LEADLESS CARDIAC PACING DEVICE WITH HELIX FIXATION

CROSS-REFERENCE TO RELATED PATENT DOCUMENTS

This application claims the benefit of and priority to U.S. Provisional Patent Application No. 62/898,701, filed on Sep. 11, 2019 and titled TOOLS AND SYSTEMS FOR IMPLANTING AND/OR RETRIEVING A LEADLESS CARDIAC PACING DEVICE WITH HELIX FIXATION, this disclosure of which is incorporated by reference.

TECHNICAL FIELD

The present disclosure pertains to medical devices, and methods for manufacturing and/or using medical devices. More particularly, the present disclosure pertains to leadless cardiac devices and methods, such as leadless cardiac pacing devices and methods, and delivery and retrieval devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

In one example, an implantation and/or retrieval device for a leadless cardiac pacing device may comprise: a first elongate shaft including a lumen; a second elongate shaft slidably disposed within the lumen of the first elongate shaft; an end cap assembly fixedly attached to a distal end of the first elongate shaft; and a plurality of wires attached to the second elongate shaft and extending distally from the end cap assembly, the plurality of wires being movable relative to the end cap assembly. The plurality of wires is configured to engage a proximal hub of the leadless cardiac pacing device. The plurality of wires forms a plurality of wire loops extending distally from the end cap assembly.

In addition or alternatively, the end cap assembly includes an insert secured within an outer housing, the outer housing being fixedly attached to the distal end of the first elongate shaft.

In addition or alternatively, a distalmost surface of the insert is flush with a distalmost end surface of the outer housing.

In addition or alternatively, the insert includes a plurality of bores extending through the insert, wherein the plurality of bores is configured to receive the plurality of wires.

In addition or alternatively, each of the plurality of bores curves radially outwardly in a distal direction.

In addition or alternatively, the insert is a unitary structure.

In addition or alternatively, the insert comprises a plurality of insert members, each insert member including at least a portion of one or more of the plurality of bores extending through the insert member.

In addition or alternatively, each of the plurality of bores is configured to receive more than one of the plurality of wires.

In addition or alternatively, circumferentially adjacent wire loops of the plurality of wire loops crisscross each other when viewed axially.

In addition or alternatively, an implantation and/or retrieval device for a leadless cardiac pacing device may comprise: a first elongate shaft including a lumen; an end cap assembly fixedly attached to a distal end of the first elongate shaft; and a plurality of wires extending through the end cap assembly and forming a plurality of wire loops distal of the end cap assembly, the plurality of wires being movable through the end cap assembly between a first position and a second position distal of the first position. The plurality of wire loops is configured to secure the proximal hub of the leadless cardiac pacing device relative to the end cap assembly in the first position.

In addition or alternatively, the end cap assembly includes an insert secured within an outer housing. The insert may include a distalmost surface that is flush with a distalmost surface of the outer housing, and a plurality of bores extending through the insert and opening distally. The plurality of wire loops is configured to secure the proximal hub of the leadless cardiac pacing device against the distalmost surface of the insert in the first position.

In addition or alternatively, circumferentially adjacent wire loops of the plurality of wire loops crisscross each other when viewed axially.

In addition or alternatively, the plurality of wires is configured to transfer rotational motion of the first elongate shaft to the proximal hub in the first position.

In addition or alternatively, the plurality of wire loops includes a first wire loop passing through a first pair of the plurality of bores, a second wire loop passing through a second pair of the plurality of bores, and a third wire loop passing through a third pair of the plurality of bores.

In addition or alternatively, one of the second pair of the plurality of bores is disposed circumferentially between the first pair of the plurality of bores, and one of the third pair of the plurality of bores is disposed circumferentially between the second pair of the plurality of bores.

In addition or alternatively, a distal end segment of the first wire loop is parallel to a distal end segment of the third wire loop, and the distal end segment of the first wire loop is perpendicular to a distal end segment of the second wire loop.

In addition or alternatively, system may comprise: a leadless cardiac pacing device including a body, a proximal hub, and a helical fixation member opposite the proximal hub; a catheter; a first elongate shaft slidably disposed within the catheter, the first elongate shaft including a lumen and a proximal handle; a second elongate shaft slidably disposed within the lumen of the first elongate shaft; an end cap assembly including an outer housing fixedly attached to a distal end of the first elongate shaft and an insert secured within the outer housing; and a plurality of wires fixedly attached to the second elongate shaft and extending distally from the end cap assembly to form a plurality of wire loops translatable between a first position and a second position distal of the first position. The plurality of wire loops is configured to engage the proximal hub of the leadless cardiac pacing device in the first position.

In addition or alternatively, the end cap assembly is devoid of any structure configured to engage a side surface of the proximal hub.

In addition or alternatively, the plurality of wires is configured to transfer rotational motion of the first elongate shaft to the proximal hub in the first position.

In addition or alternatively, the leadless cardiac pacing device includes a neck portion extending longitudinally from the body to the proximal hub. In the first position, the plurality of wire loops includes three or more intersecting distal end segments forming a bounded opening receiving the neck portion therethrough.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which:

FIG. 4A illustrates an end view of a portion of the system as seen along line 4-4 in FIG. 3A;

Figure 1:
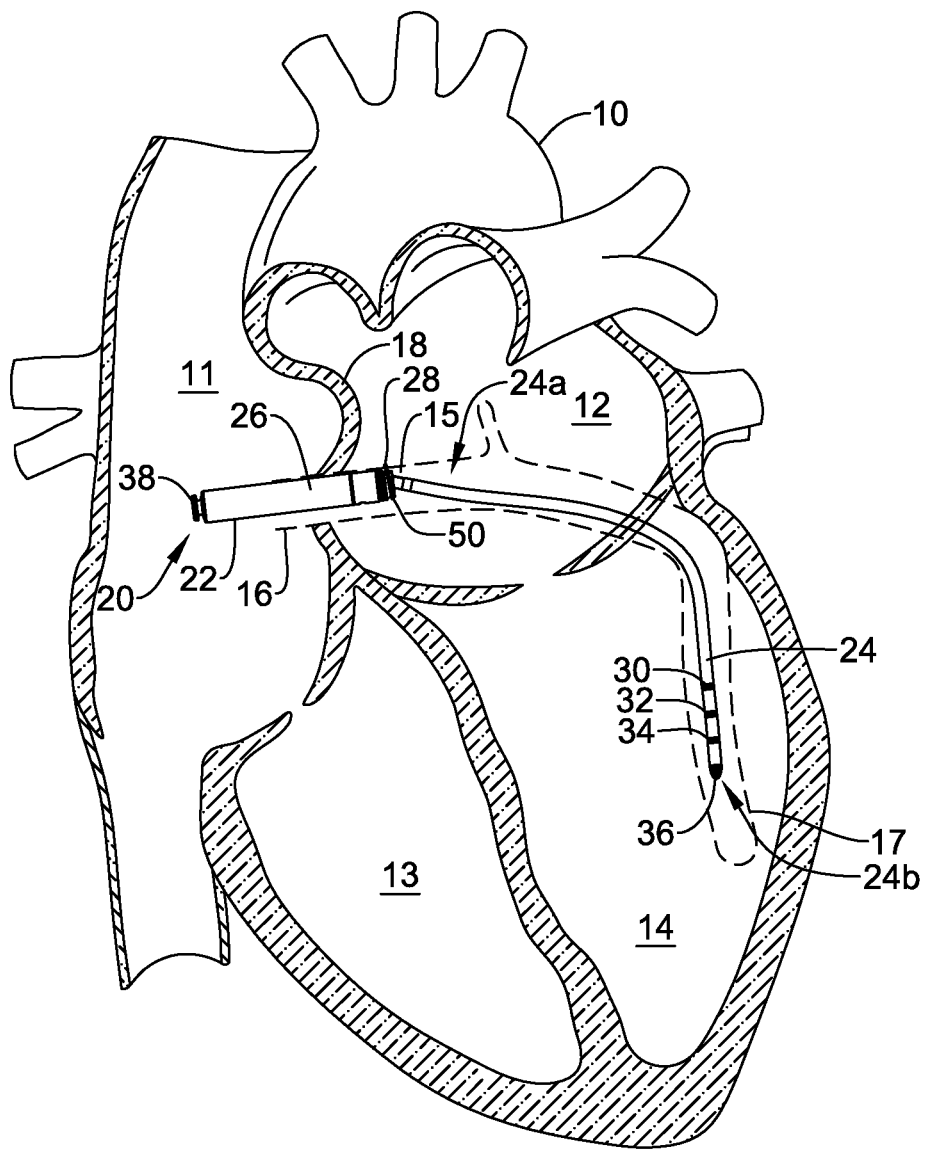
FIG. 1 is a schematic diagram of an example leadless cardiac pacing device implanted within a heart.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in or around a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. In some cases, the leadless cardiac pacemakers may include a proximal and/or a distal extension extending from the small capsule, where the extension(s) may include one or more pacing/sensing electrodes. The capsule may be delivered to the heart using a delivery device which may be advanced through a femoral vein, into the inferior vena cava, into the right atrium, and into the coronary sinus and vessels extending through and/or to the coronary sinus. Accordingly, it may be desirable to provide cardiac pacing devices and delivery devices which facilitate advancement through the vasculature.

The leadless cardiac pacing device described herein may detect and treat cardiac arrhythmias, and more particularly, deliver electrical stimulation therapy to a right atrium, left atrium, right ventricle, and/or a left ventricle of a heart of a patient. For instance, one or more devices may be implanted on or within a patient's heart, and the one or more devices may be configured to deliver electrical stimulation therapy to one or more chambers of the patient's heart in accordance with one or more therapy programs and/or to treat one or more types of detected cardiac arrhythmias. Some example electrical stimulation therapies include bradycardia therapy, cardiac resynchronization therapy (CRT), anti-tachycardia pacing (ATP) therapy, defibrillation and/or cardioversion therapy, and the like. Some example cardiac arrhythmias include atrial fibrillation or atrial flutter, ventricular fibrillation, and tachycardia.

Although various features of a leadless cardiac pacing device are described herein, alternative and/or additional features of an example leadless cardiac pacing device are discussed in U.S. Provisional Patent Application Ser. No. 62/826,496 entitled SYSTEMS AND METHODS FOR TREATING CARDIAC ARRHYTHMIAS filed on Mar. 29, 2019, which is hereby incorporated by reference for all purposes; and U.S. Provisional Patent Application Ser. No. 62/826,507 entitled SYSTEMS AND METHODS FOR TREATING CARDIAC ARRHYTHMIAS filed on Mar. 29, 2019, which is hereby incorporated by reference for all purposes. Hereinafter, these references incorporated by reference are referred to as the "references incorporated herein".

FIG. 1 is a conceptual diagram of an illustrative system for delivering electrical stimulation therapy to a patient's heart, including delivering electrical stimulation therapy to a right atrium, left atrium, right ventricle, and/or a left ventricle of the patient's heart. FIG. 1 shows an illustrative leadless cardiac pacing device 20 implanted in and around heart 10. Heart 10 of FIG. 1 is depicted showing a right atrium 11, a left atrium 12, a right ventricle 13, a left ventricle 14, a coronary sinus 15, a coronary sinus ostium 16, a great cardiac vein 17, and a septum 18. In FIG. 1, the coronary sinus 15 and the great cardiac vein 17 are depicted in broken lines as these features are on the posterior side of the heart 10 and would not typically be viewable from the view of FIG. 1. Although the leadless cardiac pacing device 20 is shown implanted and extending into the coronary sinus 15 and at least part of the leadless cardiac pacing device 20 typically would not be viewable from the view of FIG. 1, an entirety of the leadless cardiac pacing device 20 is depicted in solid lines for clarity purposes. In some instances, about 50% of the length of the body 22 of the leadless cardiac pacing device 20 is inserted into the coronary sinus 15, with the proximal end region of the body 22 positioned in the right atrium 11. In some instance about 25%-75% of the distalmost portion of the length of the body 22 of the leadless cardiac pacing device 20 may be inserted into the coronary sinus 15, with the remaining proximal end region of the body 22 positioned in the right atrium 11.

In the example of FIG. 1, the leadless cardiac pacing device 20 includes a body 22 having a proximal end and a distal end and a distal extension 24 extending distally of the distal end of the body 22. However, in some instances, the distal extension 24 may not be included and/or one or more other distal and/or proximal extensions may be included. The body 22 need not have the same cross-sectional shape along its entire length. When implanted, the body 22 may be fully or partially disposed within the coronary sinus 15 of the patient's heart 10, while the distal extension 24 may be fully or partially disposed within a vessel extending from the coronary sinus 15 (e.g., the great cardiac vein 17, an anterior interventricular vein, another laterally descending vessel, etc.).

The body 22 may have any dimension suitable for implantation at a target location within the heart 10 of a patient. In one example, the body 22 may have a cross-sectional diameter or area sufficient to fit within the coronary sinus 15, which may vary between about 0.24 inches (6 mm) to about 0.6 inches (15 mm). A diameter of the body 22 may range, in different embodiments, between about 0.1 inches (2.54 mm) to about 0.4 inches (10 mm). The body 22 may be sized to be implanted within different sized coronary sinuses while still allowing sufficient blood flow through the coronary sinus 15.

In some embodiments, the leadless cardiac pacing device 20 may include one or more electrodes. In one example, the body 22 of the leadless cardiac pacing device 20 may support a first electrode 26 and a second electrode 28, while the distal extension 24 may support a distal electrode. In some cases, the distal extension 24 may include a plurality of electrodes (e.g., a first proximal ring electrode 30, a second proximal ring electrode 32, a third proximal ring electrode 34, a distal ring electrode 36, and/or one or more other electrodes). Although the electrodes described may be indicated as being ring electrodes, other electrode types may be utilized depending on the application.

In some cases, the first electrode 26 may be formed on, along, and/or from the body 22 and the second electrode 28 may be formed on, along, and/or from a fixation member 50 (discussed in greater detail below) extending from the body 22. In one example, the body 22 may be at least partially formed from an electrically conductive material and an exposed surface of such electrically conductive material may form, at least in part, the first electrode 26. Additionally, or alternatively, the second electrode 28 may be formed from one or more exposed electrically conductive surface portions of the fixation member 50 that may be exposed to cardiac tissue of the patient. Various arrangements for the electrodes 26, 28, including location, shape, material(s), etc. are contemplated. Alternative and/or additional electrode configurations for a leadless cardiac pacing device 20 are discussed in the references incorporated herein.

When provided, the electrodes of the leadless cardiac pacing device 20 may be used to deliver electrical stimulation to heart 10, and/or sense one or more physiologic signals. In some cases, the leadless cardiac pacing device 20 may use one or more of the electrodes (e.g., electrodes 26-36 or other electrodes) to communicate with one or more other devices, such as, but not limited to, one or more other leadless cardiac pacemakers and/or an implantable cardioverter defibrillator. In some instances, the leadless cardiac pacing device 20 may communicate using conducted communication techniques and may deliver and/or receive communication signals through one or more of the electrodes (e.g., the electrodes 26-36 or other electrodes). In some embodiments, the leadless cardiac pacing device 20 may include one or more communication wires configured to operate as antenna for wireless communication with and/or to receive electrical energy from one or more other devices.

In some instances, the leadless cardiac pacing device 20 may include a neck portion extending longitudinally from the body 22 to a proximal hub 38 (e.g., a docking hub or other member) disposed generally proximal of the body 22. During implantation, the proximal hub 38 may be releasably coupled to an implantation and/or retrieval device (not shown in FIG. 1). When coupled, movement of the implantation and/or retrieval device may translate to the leadless cardiac pacing device 20 and/or the body 22, thereby allowing a user, such as a physician, to maneuver the leadless cardiac pacing device 20 and/or the body 22 into position within the heart 10, for example into or proximate the coronary sinus 15. The implantation and/or retrieval device may be capable of longitudinally and/or rotationally manipulating the leadless cardiac pacing device 20.

In some instances, the leadless cardiac pacing device 20 may be delivered from a delivery catheter (not shown in FIG. 1), and the portion of the delivery catheter surrounding the body 22 may conform to the body 22 to create a secure connection between the delivery catheter and the body 22. When the leadless cardiac pacing device 20 is in position, the delivery catheter may be retracted, or the implantation and/or retrieval device may be used to push the body 22 out of the delivery catheter and/or otherwise adjust a position of the leadless cardiac pacing device 20. In some embodiments, the implantation and/or retrieval device may apply rotational torque to the body 22 to anchor the leadless cardiac pacing device 20 to cardiac tissue.

Although the distal extension 24 is depicted in FIG. 1, in some instances, the leadless cardiac pacing device 20 may not include the distal extension 24. Where the leadless cardiac pacing device 20 includes the distal extension 24, the distal extension 24 may extend distally from the distal end of the body 22. Further, when included, the distal extension 24 may extend into the coronary sinus 15 and be secured within the coronary sinus 15. In some cases, the distal extension 24 may extend through the coronary sinus 15 and into the great cardiac vein 17, as depicted in FIG. 1, or one or more other vessels extending from the coronary sinus 15 or great cardiac vein 17.

The distal extension 24 may include a proximal end 24a and a distal end 24b. The distal end 24b of the distal extension 24 may include one or more engaging members, but this is not required. The engaging members, when included, may help secure the distal end 24b of the distal extension 24 within the coronary sinus 15 or the great cardiac vein 17, and/or may include one or more electrodes or wire loops and may act as an antenna to communicate with and/or receive electrical energy from one or more other devices. For example, the leadless cardiac pacing device 20 may receive an energy transfer and/or communicate using inductive and/or conductive communication techniques through electrodes and/or wire loops of the engaging member.

In some embodiments, the electrodes 30-36 on the distal extension 24 may be used to deliver electrical stimulation to the heart 10. For example, the leadless cardiac pacing device 20 may deliver electrical stimulation to the left ventricle 14 of heart 10 through a set of one or more of electrodes (e.g., a set from the electrodes 30-36 or other electrodes). In some embodiments, the leadless cardiac pacing device 20 may deliver electrical stimulation to the left ventricle 14 of the heart 10 using two or more of the electrodes 30-36 either simultaneously or with a delay (e.g. via multi-electrode pacing). In some embodiments, the leadless cardiac pacing device 20 may use one or more of the electrodes 30-36 to communicate with one or more other devices (e.g., the electrodes 30-36 may act as an antenna). For example, the leadless cardiac pacing device 20 may receive an energy transfer and/or communicate using inductive or conductive communication techniques through one or more of the electrodes 30-36.

The electrodes 26-36 and/or other electrodes on the leadless cardiac pacing device 20 may be able to sense electrical signals, provide electrical stimulation signals, or sense electrical signals and provide electrical stimulation signals. Signal processing, communication, and/or therapy pulse generation may take place at any portion of the leadless cardiac pacing device where the appropriate processing modules may be located. In one example, signal processing, communication, and therapy pulse generation for the electrodes (e.g., electrodes 26-36 and/or other electrodes) of the leadless cardiac pacing device 20 may take place in modules within or supported by the body 22.

In some embodiments, the leadless cardiac pacing device 20 may be implanted as a single device (e.g., without additional leadless cardiac pacing devices or one or more implantable cardioverter defibrillators), which may provide electrical stimulation to the right atrium 11, the left atrium 12, right ventricle 13, and/or the left ventricle 14, as desired. For example, the leadless cardiac pacing device 20 may be configured to deliver electrical stimulation in accordance with a therapy program to treat atrial fibrillation or atrial flutter. In other cases, the leadless cardiac pacing device 20 may be implanted with other leadless cardiac pacing devices and/or one or more implantable cardioverter defibrillators implanted at one or more locations in and/or around the heart 10.

Figure 2:
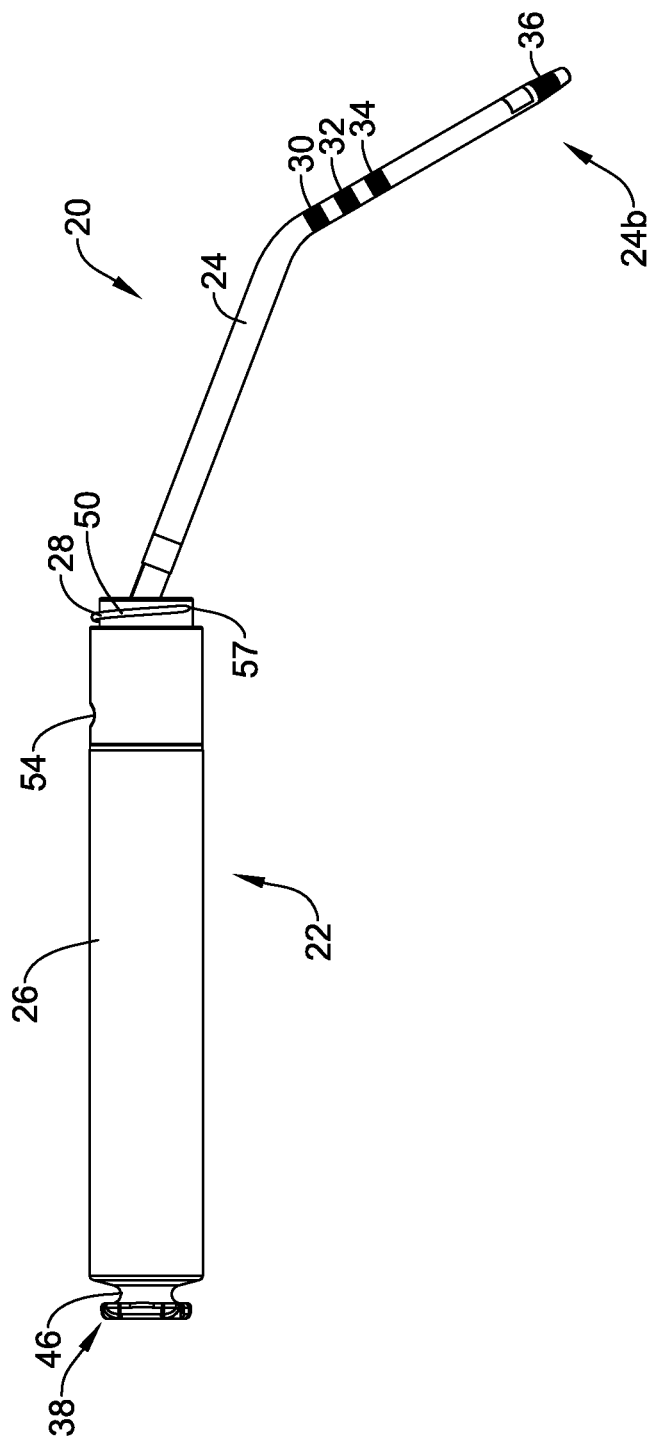
FIG. 2 is a side view of an example implantable leadless cardiac pacing device.

FIG. 2 is a schematic diagram of the illustrative leadless cardiac pacing device 20. In some embodiments, the body 22 may generally include a biocompatible material, such as a biocompatible metal and/or polymer, and may hermetically seal the components of the leadless cardiac pacing device 20 against fluid intrusion. The body 22 depicted in FIG. 2 may have a generally straight elongated shape extending along a central longitudinal axis. In some instances, the body 22 may be substantially cylindrical. The body 22, however, may take on one or more other suitable shapes including, but not limited to, having a bent or angled portion to facilitate engaging tissue of the heart 10 with electrodes of the leadless cardiac pacing device 20. Additional or alternative shape configurations for the body 22 are discussed in the references incorporated herein.

As discussed above, the leadless cardiac pacing device 20 may have one or more electrodes, such as electrodes 26, 28 and/or other electrodes, which in the example shown, are supported by the body 22 as described herein. It is contemplated in some cases that the body 22 may have a different number of electrodes, or no electrodes at all.

In some embodiments, the leadless cardiac pacing device 20 may include a neck portion 46 extending from a proximal end of the body 22 to the proximal hub 38. In some cases, the neck portion 46 may have a first outer extent and a proximal end of the neck portion 46 may be connected to the proximal hub 38 having a second outer extent. In some examples, the second outer extent of the proximal hub 38 may be greater than the first outer extent of the neck portion 46. Other configurations are also contemplated.

During implantation, as discussed in greater detail below with respect to FIGS. 12-20, an implantation and/or retrieval device (e.g., FIG. 3) may releasably engage with and/or couple to the proximal hub 38. When coupled, movement of the implantation and/or retrieval device may transfer to the body 22, thereby allowing a user to longitudinally position and/or rotate the leadless cardiac pacing device 20 during implantation. In some cases, instead of or in addition to the neck portion 46 and the proximal hub 38, the leadless cardiac pacing device 20 may include one-half of an interlocking mechanism, and the implantation and/or retrieval device may have the second half of the interlocking mechanism, which may releasably couple to the interlocking mechanism of the leadless cardiac pacing device 20. Interlocking mechanisms may be configured to create a magnetic connection, a keyed connection, and/or other suitable connections. Additional and/or alternative interlocking mechanisms are described in the references incorporated herein.

In some instances, the body 22 may include the fixation member 50 and/or the fixation member 50 may extend from the body 22 opposite the proximal hub 38. In some embodiments, the fixation member 50 may be a helical fixation member and may include a distal tip 57, as depicted in FIG. 2, and may be configured to maintain the leadless cardiac pacing device 20 within the coronary sinus 15 when the leadless cardiac pacing device 20 is implanted within the coronary sinus 15 of the heart 10. In some instances, the fixation member 50 is a helical coil that may have an outer diameter in the range of about 0.247 inches (6.274 mm) to about 0.275 inches (6.985 mm) and a pitch of about 0.050 (1.270 mm) to about 0.075 inches (1.905 mm) for at least one revolution around the helical coil, but in some embodiments, the helical fixation member 50 may take on one or more different diameters and/or a different suitable pitch. The fixation member 50 may be formed from a material having a diameter suitable for penetrating and engaging tissue of a heart, conducting electricity, and/or for being flexible or bendable. Additional dimensions and/or features of the fixation member 50 are described in the references incorporated herein.

The fixation member 50 may be secured to the body 22 in any suitable manner. In one example, a proximal portion of the fixation member 50 (e.g., a proximal portion of the helical coil) may be embedded (e.g., molded) within the body 22 and a distal portion (e.g., a distal portion of the helical coil) of the fixation member 50 may extend from the body 22 and may be configured to engage cardiac tissue of the patient when the leadless cardiac pacing device is positioned in the patient. The distal portion of the fixation member 50 may be configured to extend about 0.5 revolutions to about 2.0 revolutions (or any amount therebetween) about the body 22. The fixation member 50 may be configured, at least in part, from a material that is configured to penetrate and engage tissue of a heart, that is electrically conductive, that is radiopaque, and/or that is flexible and/or has shape memory properties. Some suitable but non-limiting examples of materials for the fixation member 50 are described below.

In some cases, the fixation member 50 may be able to straighten or elongate from the helical configuration when the fixation member 50 is engaging tissue and an axial force is applied to the leadless cardiac pacing device 20. In some instances, the fixation member 50 may be plastically deformed and elongated into a straightened configuration from its helical configuration when subjected to an axial force. Such a configuration of the fixation member 50 may facilitate removal of the leadless cardiac pacing device 20 and may reduce risk causing damage to the patient due to perforation or bruising.

Although one fixation member 50 is depicted on the body 22 in the Figures, the body 22 may support one or more additional fixation members that are axially spaced from the fixation member 50. In other instances, the body 22 may not include a fixation member 50. In some cases, as discussed above, the fixation member 50 may include or form one or more electrodes (e.g., the second electrode 28 or other suitable electrode) and/or may act as an antenna to communicate with and/or receive electrical energy from one or more other devices. For example, the leadless cardiac pacing device 20 may receive an energy transfer and/or communicate using inductive and/or conductive communication techniques through electrodes of the fixation member 50.

In at least some cases, the body 22 may have a guide wire port 54 extending through and/or opening out to a side of the body 22, where the side extends from a first end to a second end of the body 22. In some cases, the guide wire port 54 may be configured to receive a guide wire. Where the leadless cardiac pacing device 20 includes the distal extension 24, the distal extension 24 may include a corresponding guide wire port at a distal tip of the distal end 24b of the distal extension 24. In such instances, a guide wire may be placed down the great cardiac vein 17 (or other vessel in communication with the coronary sinus 15). The leadless cardiac pacing device 20 may be tracked over the guide wire by threading the distal extension 24 over a proximal end of the guide wire, and then advancing the leadless cardiac pacing device 20 over the guide wire until in position. In embodiments where the leadless cardiac pacing device 20 does not include the distal extension 24, the body 22 may include a second guide wire port.

When included, the distal extension 24 may extend from the body 22 at any suitable angle. In some cases, the distal extension 24 may extend from the body 22 at an angle relative to a central longitudinal axis of the body 22. In some embodiments, the angle may be an oblique angle, such that the distal extension 24, while in an unconstrained state with no external forces applied to bend or flex the distal extension 24, extends from the body 22 at a non-parallel angle to the central longitudinal axis of the body 22. In some instances, the oblique angle may be in the range of 10 degrees to 50 degrees. In some cases, the distal extension 24 may extend distally from the body 22 toward a circumferential side of the body 22 opposite from the guide wire port 54.

The distal extension 24 may be a thin, elongated, and flexible member, particularly in relation to the body 22. For instance, the distal extension 24 may be between two and ten times the length of the body 22. In some embodiments, the electrodes 30-36 and/or other electrodes may be disposed proximate the distal end 24b of the distal extension 24 or may be spread out along the length of distal extension 24 (e.g., longitudinally spaced from one another), as shown in FIG. 2. Other arrangements and/or configurations of electrodes on the distal extension 24 are contemplated and may be utilized. In one example arrangement, each of the electrodes may be ring electrodes and the electrode 36 (e.g., a distal ring electrode) may be disposed on the distal extension 24 near a distal tip of the distal extension 24, the electrode 34 (e.g., a third proximal ring electrode) may be spaced forty (40) millimeters proximal of the electrode 36, the electrode 32 (e.g., a second proximal ring electrode) may be spaced ten (10) millimeters proximal of the electrode 34, and the electrode 30 (e.g., a first proximal ring electrode) may be spaced ten (10) millimeters proximal of the electrode 32. Such a configuration of electrodes 30-36 may align with the left atrium 12 when the distal extension 24 is inserted into the great cardiac vein 17 or other vessel to allow the leadless cardiac pacing device 20 to sense and/or pace the left atrium 12 of the heart 10. In some cases, the distal extension 24 may be biased to form a shape such as a helical coil or one or more loops.

Figure 3:
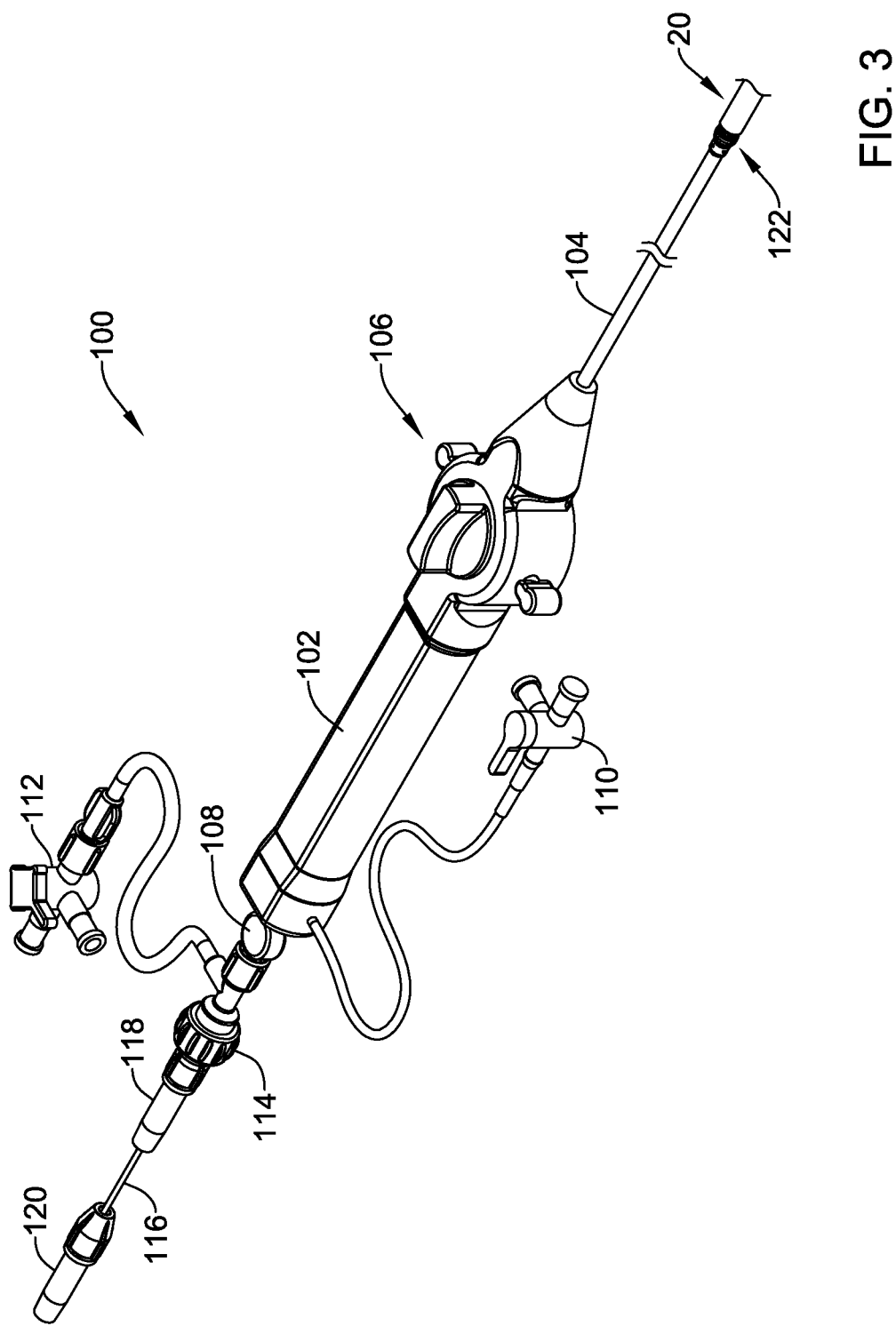
FIG. 3 illustrates aspects of a system for implantation and/or retrieval of the leadless cardiac pacing device.

FIG. 3 illustrates aspects of a system for implantation and/or retrieval of the leadless cardiac pacing device 20. In some embodiments, the system may include a catheter 80 (e.g., FIGS. 13-20) having a lumen extending therethrough. In some embodiments, the catheter 80 may be a delivery sheath, a retrieval sheath, or a combination thereof. In some embodiments, the system and/or selected components thereof may be referred to as an implantation and/or retrieval device for a leadless cardiac pacing device. Accordingly, any reference to the system, except as will be apparent, may also apply to an implantation and/or retrieval device, and vice versa. In some embodiments, not all elements described herein are necessary for the disclosed system to properly function. For example, the catheter 80 may be considered an optional element and/or feature in some embodiments.

A system 100 may include a first elongate shaft 104 including a lumen extending therethrough and extending distally from a proximal handle 102. The first elongate shaft 104 may be a tubular member and/or may be annular with a wall defining the lumen extending therethrough. The first elongate shaft 104 may be slidably disposed within the lumen of the catheter 80. The proximal handle 102 may include one or more actuation elements 106 configured to deflect and/or steer a distal end of the first elongate shaft 104, from side to side for example. In one example configuration, movement and/or translation (e.g., longitudinal, rotational, etc.) of the one or more actuation elements 106 may change tension characteristics applied to the first elongate shaft 104, such as by a pull wire or other suitable means. Other means of steering the first elongate shaft 104 are also contemplated. Some suitable, but non-limiting, examples of materials for the proximal handle 102, the first elongate shaft 104, and/or the one or more actuation elements 106 are discussed below.

In some embodiments, the system 100 may include an elongate member 108 slidably disposed within the lumen of the first elongate shaft 104. In FIG. 3, only a proximal end of the elongate member 108 is visible. The elongate member 108 may be tubular in construction and may include a lumen extending therethrough. The elongate member 108 may be sized and configured to extend distally through the proximal handle 102 and into the first elongate shaft 104. In some embodiments, a distal end of the elongate member 108 may be positioned proximate the distal end of the first elongate shaft 104. Since the elongate member 108 is slidable relative to the first elongate shaft 104, the exact positioning of the elongate member 108 with respect to the first elongate shaft 104 may be varied according to need. In some embodiments, the elongate member 108 may serve as a stiffening device within the first elongate shaft 104. In some embodiments the elongate member 108 may reduce and/or prevent axial collapse, shortening, prolapse, and/or compression of the first elongate shaft 104 and/or another element that may be slidably disposed within the lumen of the elongate member 108 (such as the second elongate shaft described herein) when it is under tension, torque, compression, etc. In some embodiments, the elongate member 108 may have a greater column strength and/or a greater axial and/or lateral stiffness than the first elongate shaft 104 and/or another element slidably disposed within the elongate member 108 (e.g., the second elongate shaft). Some suitable, but non-limiting, examples of materials for the elongate member 108 are discussed below.

In some embodiments, the system 100 may include one or more irrigation ports. In one example, the system 100 may include a first irrigation port 110 fluidly connected to the proximal handle 102 and configured to irrigate and/or flush the lumen of the first elongate shaft 104. With the elongate member 108 in place within the lumen of the first elongate shaft 104, the first irrigation port 110 may be configured to irrigate and/or flush between an outer surface of the elongate member 108 and an inner surface of the lumen of the first elongate shaft 104. In some embodiments, the system 100 may include a second irrigation port 112 fluidly connected to the elongate member 108 and configured to irrigate and/or flush the lumen of the elongate member 108. In at least some embodiments, both the first irrigation port 110 and the second irrigation port 112 may be present and/or utilized. In some embodiments, neither of the first irrigation port 110 and the second irrigation port 112 may be present and/or utilized. Additional and/or other irrigation ports may be added and/or used as needed. In some embodiments, the system 100 may include a proximal port 114. In some embodiments, the proximal port 114 may be and/or may include a sealing structure configured to prevent fluid communication with an interior of the proximal handle 102 and/or the lumen of the first elongate shaft 104, and/or fluid leakage therefrom. Some suitable, but non-limiting, examples of materials for the first irrigation port 110, the second irrigation port 112, and/or the proximal port 114 are discussed below.

The system 100 may include a second elongate shaft 116 slidably disposed within the lumen of the first elongate shaft 104 and/or the elongate member 108. In some embodiments, the second elongate shaft 116 may include a first proximal handle 118 disposed proximal of the proximal port 114 and/or the proximal handle 102. In some embodiments, the second elongate shaft 116 may include a second proximal handle 120 disposed proximal of the first proximal handle 118. In some embodiments, the second proximal handle 120 may be fixedly attached to the second elongate shaft 116 at and/or proximate a proximal end of the second elongate shaft 116. The first proximal handle 118 may be slidable on the second elongate shaft 116 and may selectively lockable to the second elongate shaft 116 at a variable position along the second elongate shaft 116 selected by the user. In some embodiments, locking the first proximal handle 118 to the second elongate shaft 116 may limit axial movement of the second elongate shaft 116 relative to the handle 102, the first elongate shaft 104, the elongate member 108, and/or the proximal port 114. For example, when the first proximal handle 118 is locked to the second elongate shaft 116, the first proximal handle 118 may contact and/or interfere with the proximal port 114 (or a proximal surface of the proximal handle 102 and/or the elongate member 108, where present), thereby preventing further distal translation of the second elongate shaft 116 relative to the handle 102, the first elongate shaft 104, the elongate member 108, and/or the proximal port 114. Additional and/or other reasons for locking the first proximal handle 118 to the second elongate shaft 116 will become apparent. In at least some embodiments, the second elongate shaft 116 may be a tubular member, such as a hypotube or other similar structure, having a lumen extending therethrough. In some embodiments, the second elongate shaft 116 may be a solid shaft or wire devoid of any lumens disposed therein. Some suitable, but non-limiting, examples of materials for the second elongate shaft 116, the first proximal handle 118, and/or the second proximal handle 120 are discussed below.

Figure 3A:
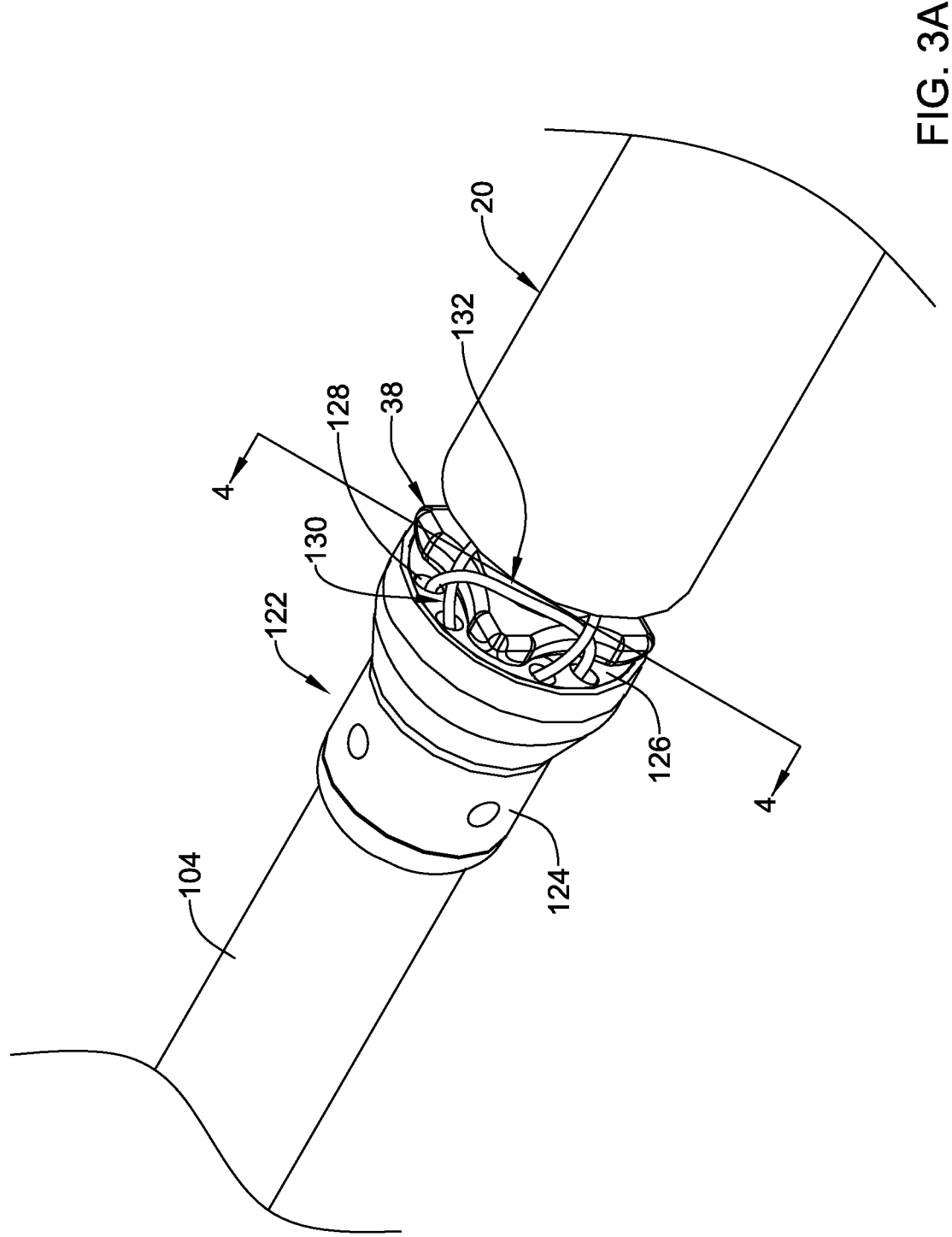
FIG. 3A is a detailed view of a portion of the system of FIG. 3.

The system 100 may include an end cap assembly 122 disposed at a distal end of the first elongate shaft 104. In some embodiments, the end cap assembly 122 may include an outer housing 124 fixedly attached to the distal end of the first elongate shaft 104 and an insert 126 secured within the outer housing 124, as shown in FIG. 3A. In some embodiments, a distalmost surface of the insert 126 is flush with a distalmost end surface of the outer housing 124. In some embodiments, the distalmost surface of the insert 126 is parallel and/or coplanar with the distalmost end surface of the outer housing 124. In some embodiments, the insert 126 may include a plurality of bores 128 extending through the insert 126. In some embodiments, the plurality of bores 128 may be oriented and/or may extend generally longitudinally through the insert 126. In at least some embodiments, the plurality of bores 128 may open distally and/or through the distalmost surface of the insert 126. Some suitable, but non-limiting, examples of materials for the end cap assembly 122, the outer housing 124, and/or the insert 126 are discussed below.

The system 100 may include a plurality of wires 130 attached to the second elongate shaft 116 and extending distally from the end cap assembly 122. While not explicitly shown, the plurality of wires 130 may be attached (e.g., fixedly attached, welded, bonded, etc.) to the second elongate shaft 116 at a location within the lumen of the first elongate shaft 104 and/or the elongate member 108. In some embodiments, the location may be proximate the distal end of the first elongate shaft 104 and/or the elongate member 108. In some embodiments, the location may be along a middle portion (e.g., from about ¼ to about ¾ of an overall length) of the first elongate shaft 104 and/or the elongate member 108. The plurality of wires 130 may be movable relative to the end cap assembly 122 via translation and/or movement of the second elongate shaft 116 relative to the first elongate shaft 104 and/or the elongate member 108. In some embodiments, the plurality of wires 130 may be movable and/or translatable through the end cap assembly 122 between a first position (e.g., FIG. 3A) and a second position (e.g., FIG. 5A) distal of the first position. Some suitable, but non-limiting, examples of materials for the plurality of wires 130 are discussed below.

The plurality of wires 130 may be configured to engage the proximal hub 38 of the leadless cardiac pacing device 20. In some embodiments, the plurality of wires 130 may form a plurality of wire loops 132 distal of and/or extending distally from the end cap assembly 122. In some embodiments, the plurality of wire loops 132 may be translatable between a first position and a second position distal of the first position. In some embodiments, the plurality of wire loops 132 may be configured to engage the proximal hub 38 of the leadless cardiac pacing device 20 in the first position. In some embodiments, the plurality of wire loops 132 may be configured to secure the proximal hub 38 of the leadless cardiac pacing device 20 relative to the end cap assembly 122 in the first position. In some embodiments, the plurality of wire loops 132 may be configured to secure the proximal hub 38 of the leadless cardiac pacing device 20 against the distalmost surface of the insert 126 in the first position. The plurality of bores 128 may be configured to receive the plurality of wires 130. In some embodiments, the plurality of wires 130 may extend through the plurality of bores 128. In some embodiments, the plurality of wires 130 may be movable and/or translatable through the plurality of bores 128 via translation and/or longitudinal movement of the second elongate shaft 116 relative to the first elongate shaft 104 and/or the second proximal handle 120 relative to the first proximal handle 118. In some embodiments, the second proximal handle 120 may be spaced proximally apart from the first proximal handle 118 when the plurality of wires 130 and/or the plurality of wire loops 132 is in the first position (e.g., FIG. 3). In some embodiments, the plurality of wires 130 and/or the plurality of wire loops 132 is configured to transfer rotational motion of the first elongate shaft 104 to the proximal hub 38 in the first position for implantation and/or retrieval of the leadless cardiac pacing device 20.

In at least some embodiments, the configuration of FIG. 3A may be seen and/or utilized before and/or during delivery of the leadless cardiac pacing device 20, wherein the proximal hub 38 of the leadless cardiac pacing device 20 is secured relative to and/or against the end cap assembly 122 for navigation to the target site. In some embodiments, the configuration shown in FIG. 3A may be seen and/or utilized during retrieval of the leadless cardiac pacing device 20, wherein the leadless cardiac pacing device 20 has been re-captured.

FIG. 4A illustrates a cross-section taken along line 4-4 in FIG. 3A. In some embodiments, each of the plurality of wire loops 132 may include and/or define a distal end segment 134. In some embodiments, the distal end segment 134 may extend between a pair (e.g., two) of the plurality of bores 128. In some embodiments, the distal end segment 134 may be substantially straight. In some embodiments, the distal end segment 134 may extend generally parallel to the distalmost surface of the insert 126 and/or the distalmost end surface of the outer housing 124. In some embodiments, the distal end segment 134 may extend generally perpendicular to the central longitudinal axis of the first elongate shaft 104 and/or the end cap assembly 122.

In some embodiments, in the first position, the plurality of wire loops 132 may include three or more intersecting distal end segments 134 forming a bounded opening 136 receiving the neck portion 46 of the leadless cardiac pacing device 20 therethrough. In some embodiments, in the first position, the bounded opening 136 may have a smallest radial extent measured perpendicular to the central longitudinal axis of the end cap assembly 122 that is greater than a greatest radial extent of the neck portion 46 measured perpendicular to the central longitudinal axis of the leadless cardiac pacing device 20, and the bounded opening 136 may have a greatest radial extent measured perpendicular to the central longitudinal axis of the end cap assembly 122 that is less than a smallest radial extent of the proximal hub 38 measured perpendicular to the central longitudinal axis of the leadless cardiac pacing device 20.

In some embodiments, circumferentially adjacent wire loops and/or distal end segments of the plurality of wire loops 132 crisscross (e.g., cross over and/or under) each other when viewed axially along the central longitudinal axis of the end cap assembly 122. In some embodiments, when the plurality of wires 130 and/or the plurality of wire loops 132 is in the first position, circumferentially adjacent wire loops of the plurality of wire loops 132 crisscross (e.g., cross over and/or under) each other when viewed axially along the central longitudinal axis of the end cap assembly 122. In some embodiments, when the plurality of wires 130 and/or the plurality of wire loops 132 is in the second position, circumferentially adjacent wire loops of the plurality of wire loops 132 crisscross (e.g., cross over and/or under) each other when viewed axially along the central longitudinal axis of the end cap assembly 122.

In some embodiments, the plurality of wire loops 132 may include a first wire loop 140 passing through a first pair 142 of the plurality of bores 128. In some embodiments, the plurality of wire loops 132 may include a second wire loop 144 passing through a second pair 146 of the plurality of bores 128. In some embodiments, the plurality of wire loops 132 may include a third wire loop 148 passing through a third pair 150 of the plurality of bores 128. In some embodiments, the plurality of wire loops 132 may include a fourth wire loop 152 passing through a fourth pair 154 of the plurality of bores 128. Other configurations and/or arrangements are also contemplated.

In some embodiments, one of the second pair 146 of the plurality of bores 128 may be disposed circumferentially between the first pair 142 of the plurality of bores 128. In some embodiments, one of the third pair 150 of the plurality of bores 128 may be disposed circumferentially between the second pair 146 of the plurality of bores 128. In some embodiments, one of the fourth pair 154 of the plurality of bores 128 may be disposed circumferentially between the third pair 150 of the plurality of bores 128. In some embodiments, one of the first pair 142 of the plurality of bores 128 may be disposed circumferentially between the fourth pair 154 of the plurality of bores 128. Other configurations and/or arrangements are also contemplated.

In the example of FIG. 4A, the plurality of wire loops 132 and/or the distal end segments 134 thereof may form an "over-under" pattern with respect to each other. In the illustrated arrangement, the first wire loop 140 passes over the fourth wire loop 152 and under the second wire loop 144, the second wire loop 144 passes over the first wire loop 140 and under the third wire loop 148, the third wire loop 148 passes over the second wire loop 144 and under the fourth wire loop 152, and the fourth wire loop 152 passes over the third wire loop 148 and under the first wire loop 140. The first wire loop 140, the second wire loop 144, the third wire loop 148, and the fourth wire loop 152 may collectively form and/or define the bounded opening 136. In the example of FIG. 4A, the proximal hub 38 includes four "lobes" or corners and has a generally square shape with scalloped sides. In some embodiments, the bounded opening 136 may be generally square. Other configurations are also contemplated. In some embodiments, the distal end segment 134 of the first wire loop 140 may be oriented generally parallel to the distal end segment 134 of the third wire loop 148. In some embodiments, the distal end segment 134 of the second wire loop 144 may be oriented generally parallel to the distal end segment 134 of the fourth wire loop 152. In some embodiments, the distal end segment 134 of the first wire loop 140 and/or the distal end segment of the third wire loop 148 may be oriented generally perpendicular to the distal end segment 134 of the second wire loop 144 and/or the distal end segment 134 of the fourth wire loop 152. In some embodiments, adjacent bores of the plurality of bores 128 may be spaced apart by a distance less than a width and/or radial extent of the proximal hub 38. As discussed herein, the configuration of FIG. 4A may be used during delivery of the leadless cardiac pacing device 20 and/or may be used during retrieval of the leadless cardiac pacing device 20.

Figure 4B:
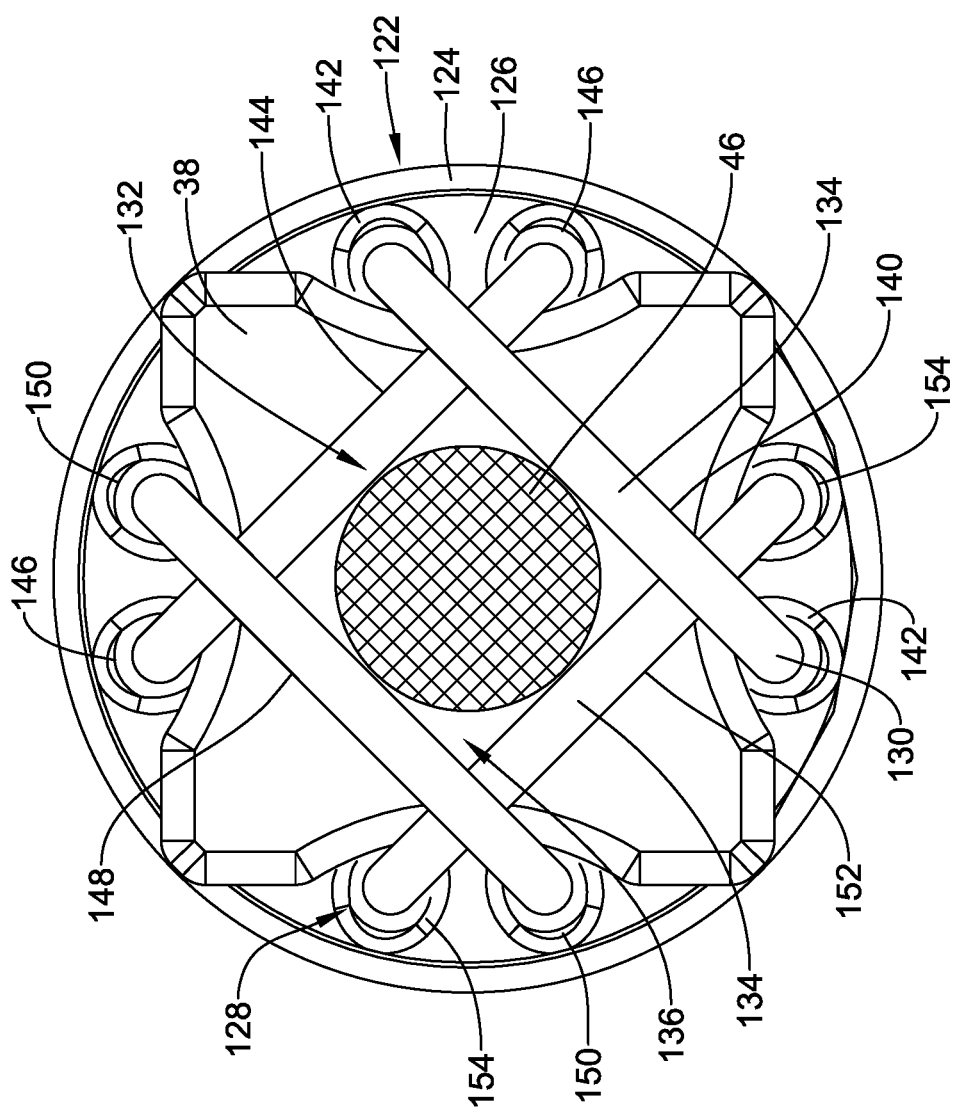
FIG. 4B illustrates an end view of a portion of an alternative configuration of the system as seen along line 4-4 in FIG. 3A.

FIG. 4B illustrates an alternative configuration of the cross-section taken along line 4-4 in FIG. 3A, which may be substantially the same as the configuration of FIG. 4A above, except that in the example of FIG. 4B, the plurality of wire loops 132 and/or the distal end segments 134 thereof may form an "over-over" and "under-under" pattern with respect to each other. In the illustrated arrangement, the first wire loop 140 passes over the fourth wire loop 152 and over the second wire loop 144, the second wire loop 144 passes under the first wire loop 140 and under the third wire loop 148, the third wire loop 148 passes over the second wire loop 144 and over the fourth wire loop 152, and the fourth wire loop 152 passes under the third wire loop 148 and under the first wire loop 140. The first wire loop 140, the second wire loop 144, the third wire loop 148, and the fourth wire loop 152 may collectively form and/or define the bounded opening 136. In the example of FIG. 4B, the proximal hub 38 includes four "lobes" or corners and has a generally square shape with scalloped sides. In some embodiments, the bounded opening 136 may be generally square. In some embodiments, the distal end segment 134 of the first wire loop 140 may be oriented generally parallel to the distal end segment 134 of the third wire loop 148. In some embodiments, the distal end segment 134 of the second wire loop 144 may be oriented generally parallel to the distal end segment 134 of the fourth wire loop 152. In some embodiments, the distal end segment 134 of the first wire loop 140 and/or the distal end segment of the third wire loop 148 may be oriented generally perpendicular to the distal end segment 134 of the second wire loop 144 and/or the distal end segment 134 of the fourth wire loop 152. In some embodiments, adjacent bores of the plurality of bores 128 may be spaced apart by a distance less than a width and/or radial extent of the proximal hub 38. As discussed herein, the configuration of FIG. 4B may be used during delivery of the leadless cardiac pacing device 20 and/or may be used during retrieval of the leadless cardiac pacing device 20.

Figure 4C:
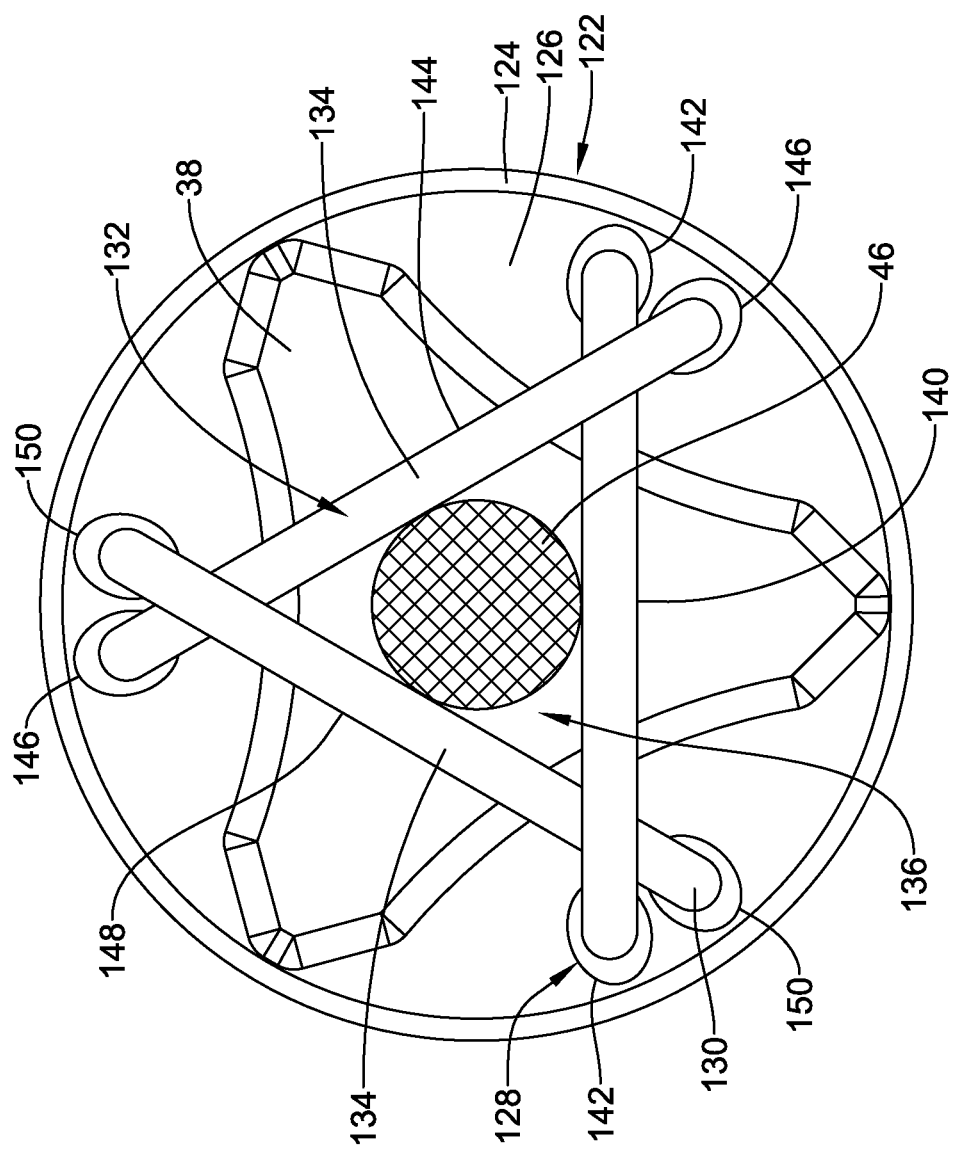
FIG. 4C illustrates an end view of a portion of an alternative configuration of the system as seen along line 4-4 in FIG. 3A.

FIG. 4C illustrates an alternative configuration of the cross-section taken along line 4-4 in FIG. 3A, which may be substantially the same as the configuration of FIG. 4A above, except that in the example of FIG. 4C, there are only three wire loops and three pairs of the plurality of bores 128. In the example of FIG. 4C, the plurality of wire loops 132 and/or the distal end segments 134 thereof may form an "over-under" pattern with respect to each other. In the illustrated arrangement, the first wire loop 140 passes over the third wire loop 148 and under the second wire loop 144, the second wire loop 144 passes over the first wire loop 140 and under the third wire loop 148, and the third wire loop 148 passes over the second wire loop 144 and under the first wire loop 140. The first wire loop 140, the second wire loop 144, and the third wire loop 148 may collectively form and/or define the bounded opening 136. The proximal hub 38 includes three "lobes" or corners and has a generally triangular shape with scalloped sides. In some embodiments, the bounded opening 136 may be generally triangular. Other configurations are also contemplated. In some embodiments, adjacent bores of the plurality of bores 128 may be spaced apart by a distance less than a width and/or radial extent of the proximal hub 38. As discussed herein, the configuration of FIG. 4C may be used during delivery of the leadless cardiac pacing device 20 and/or may be used during retrieval of the leadless cardiac pacing device 20.

Figure 5:
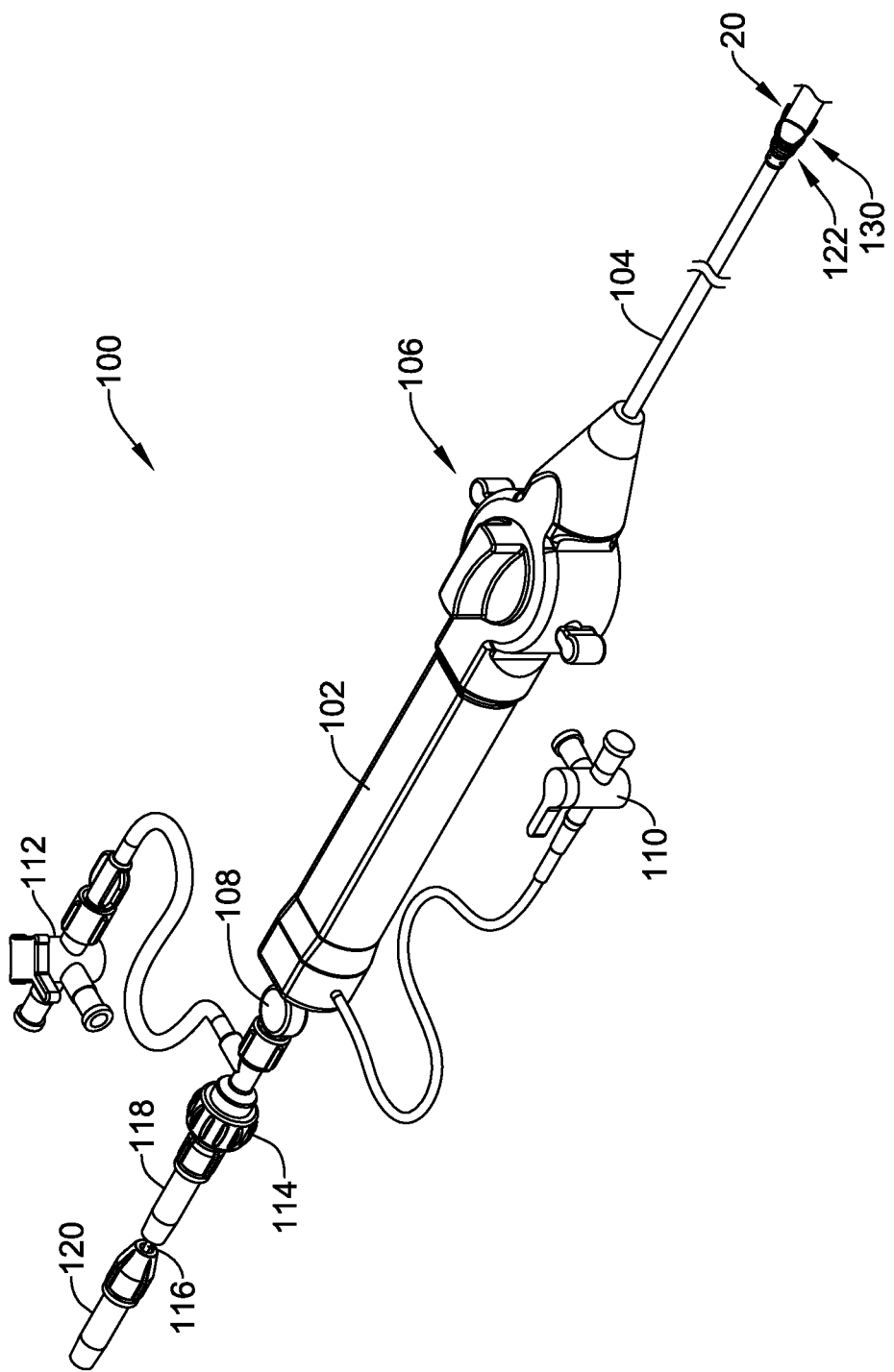
FIG. 5 illustrates aspects of the system of FIG. 3.
Figure 5A:
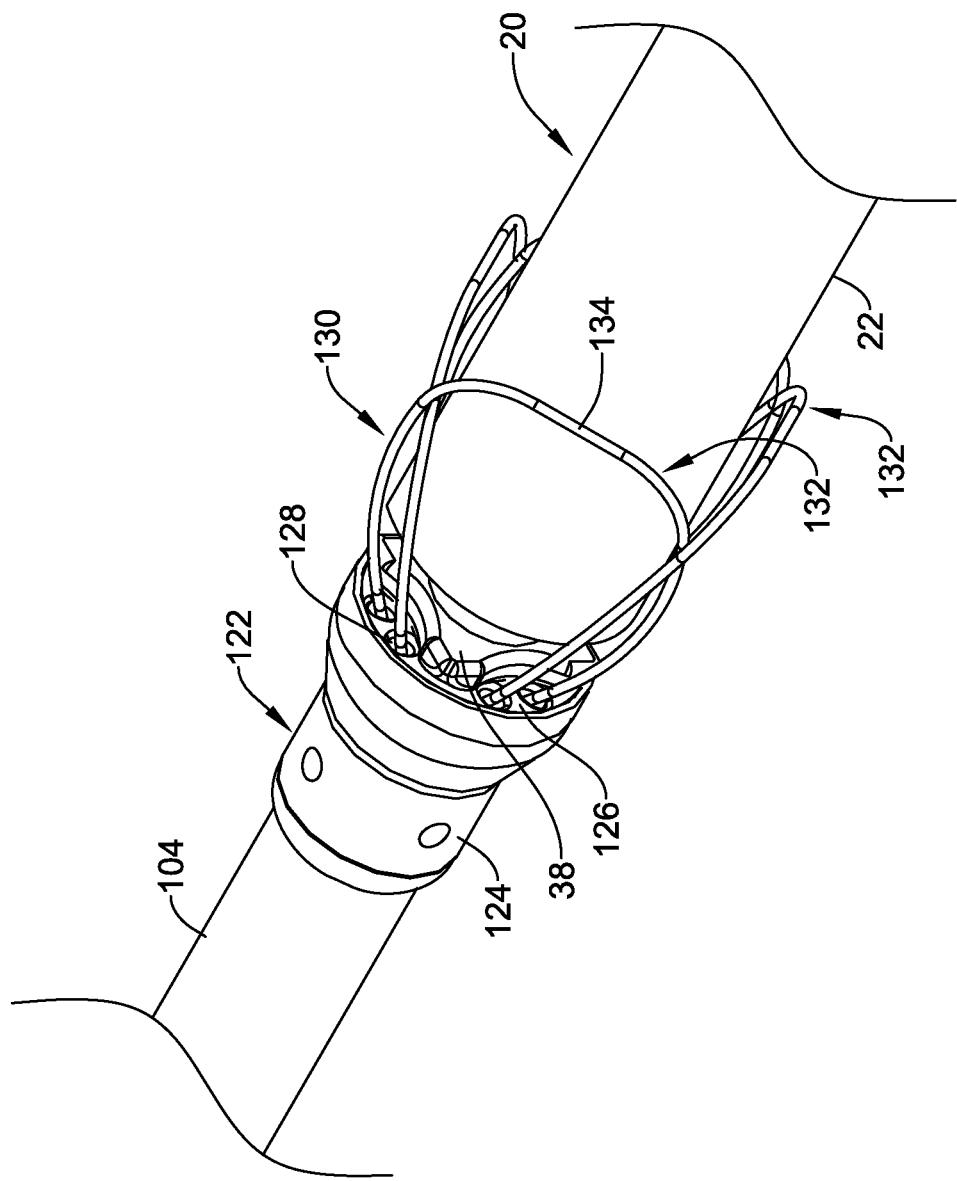
FIG. 5A is a detailed view of a portion of the system of FIG. 5.

FIGS. 5 and 5A illustrate selected aspects of the system 100 shown in FIGS. 3 and 3A. In some embodiments, the second proximal handle 120 may be moved closer to and/or into abutment with the first proximal handle 118 when the plurality of wires 130 and/or the plurality of wire loops 132 is in the second position (e.g., FIG. 5). FIG. 5A shows the plurality of wires 130 and/or the plurality of wire loops 132 in the second position in more detail. When the plurality of wires 130 and/or the plurality of wire loops 132 is in the second position, the leadless cardiac pacing device 20 may be loaded to the implantation and/or retrieval device for delivery and/or implantation to the target site, or the leadless cardiac pacing device 20 may be captured at the target site for retrieval and/or removal from the target site. The plurality of wires 130 and/or the plurality of wire loops 132, in the second position, may extend radially outward of an outermost circumference of the leadless cardiac pacing device 20 and/or the body 22. In the second position, the distal end segment 134 of each of the plurality of wire loops 132 may be substantially straight. In some embodiments, the distal end segment 134 may extend generally parallel to the distalmost surface of the insert 126 and/or the distalmost end surface of the outer housing 124. In some embodiments, the distal end segment 134 may extend generally perpendicular to the central longitudinal axis of the first elongate shaft 104 and/or the end cap assembly 122.

Figure 6:
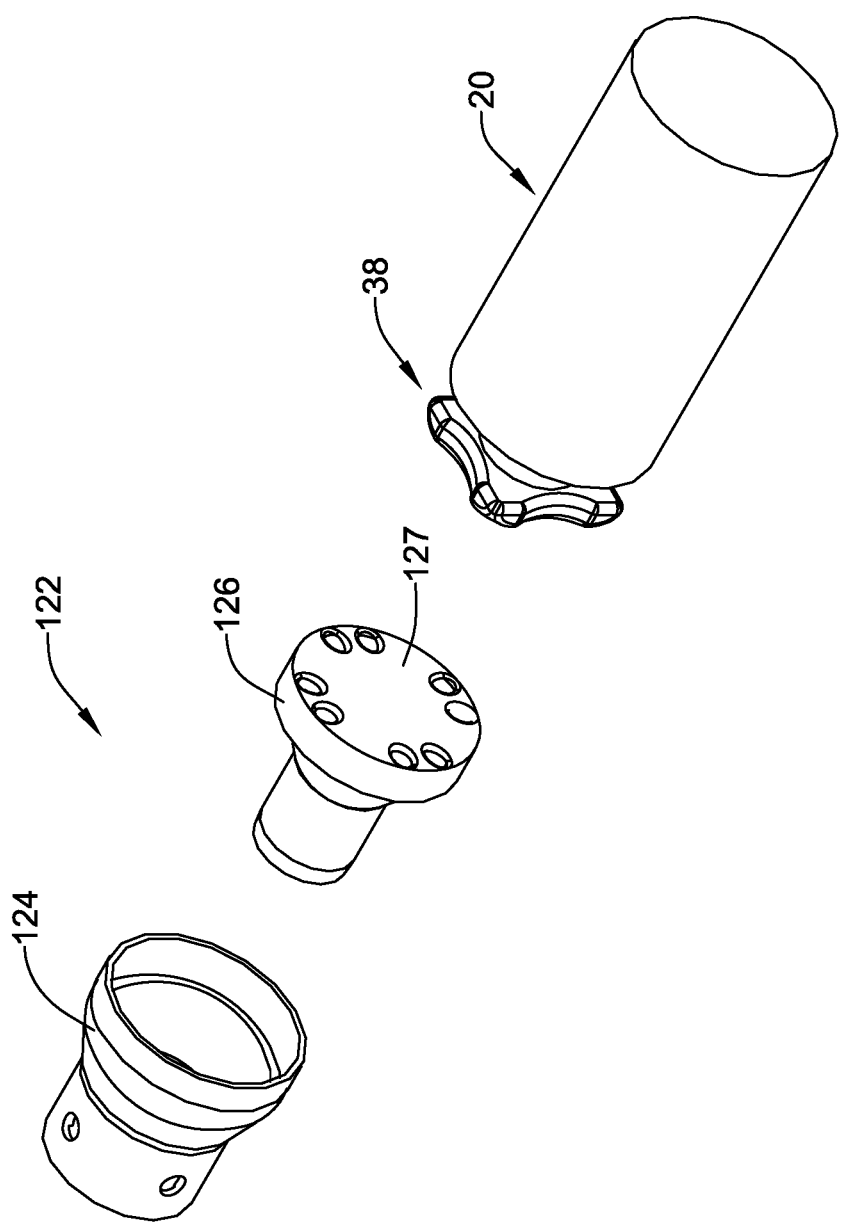
FIG. 6 is an exploded view illustrating selected aspects of the system of FIGS. 3 and 5.

FIG. 6 is an exploded view of certain elements of the system 100, for example, the end cap assembly 122 and the leadless cardiac pacing device 20 of FIGS. 3A and/or 5A. As may be seen, the end cap assembly 122 includes the outer housing 124 and the insert 126. The insert 126 may be coaxially received within the outer housing 124. In some embodiments, the insert 126 may be fixedly attached to the outer housing 124, such as by adhesive bonding, mechanical attachment, various forms of welding, or other means. In at least some embodiments, the insert 126 may be a unitary structure, as seen in FIG. 6. The insert 126 may include a distalmost surface 127 that is substantially flat and/or planar. The distalmost surface 127 of the insert 126 may be configured to abut and/or contact a proximal surface of the proximal hub 38. In at least some embodiments, the end cap assembly 122, the outer housing 124, and/or the insert 126 may be devoid of any structure configured to engage and/or contact a side surface of the proximal hub 38.

Figure 7:
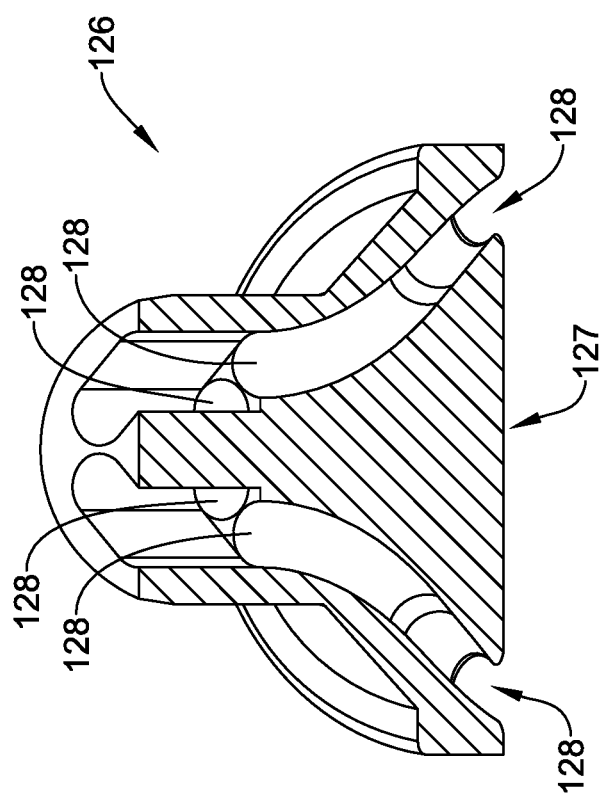
FIG. 7 is a cross-sectional view of an example insert in accordance with the disclosure.

FIG. 7 is a cross-sectional view of the insert 126 of FIG. 6. As described above, the insert 126 may include the plurality of bores 128 extending through the insert 126. In some embodiments, the plurality of bores 128 may be oriented and/or may extend generally longitudinally through the insert 126. In some embodiments, some and/or each of the plurality of bores 128 may curve radially outwardly in a distal direction relative to the central longitudinal axis of the insert 126. In at least some embodiments, the plurality of bores 128 may open distally and/or through the distalmost surface 127 of the insert 126. The plurality of wires 130 (not shown) may extend through the insert 126 and/or the plurality of bores 128. A proximal portion of the plurality of wires 130 may extend proximally from the insert 126 into the first elongate shaft 104, where the proximal portion of the plurality of wires 130 may be fixedly attached and/or joined to a distal end of the second elongate shaft 116.

Figure 8:
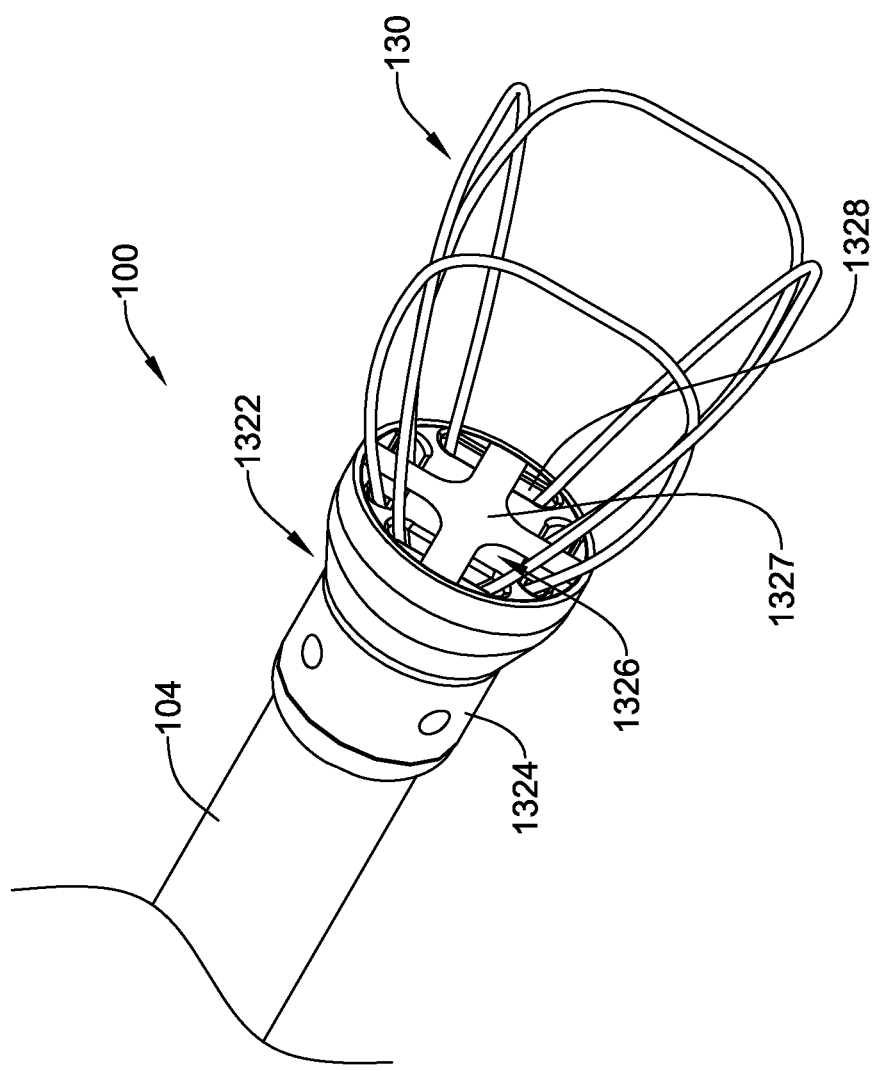
FIG. 8 illustrates aspects of an alternative configuration of the system of FIGS. 3 and 5.
Figure 9:
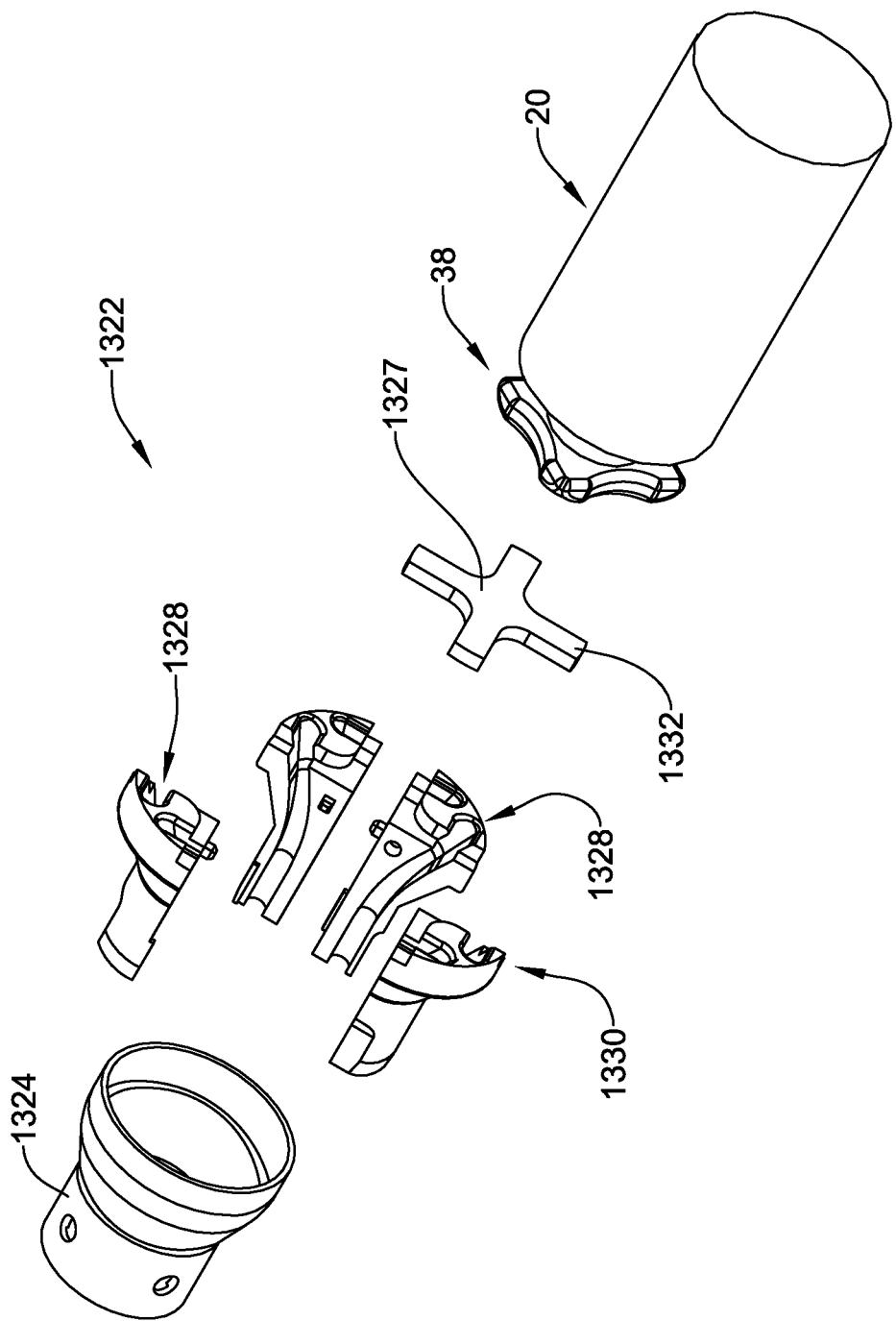
FIG. 9 is an exploded view illustrating selected aspects of the system of FIG. 8.

FIGS. 8-9 illustrate an alternative configuration of the end cap assembly 122 of FIGS. 5A-7. For reference, in the example of FIG. 8, the plurality of wires 130 is shown in the second position. In some embodiments, the system 100 may include an end cap assembly 1322, which may be similar to the end cap assembly 122 in many ways, except as expressly described herein. The end cap assembly 1322 may be disposed at the distal end of the first elongate shaft 104. In some embodiments, the end cap assembly 1322 may include an outer housing 1324 fixedly attached to the distal end of the first elongate shaft 104 and an insert 1326 secured within the outer housing 1324, as shown in FIG. 8. In some embodiments, a distalmost surface 1327 of the insert 1326 is flush with a distalmost end surface of the outer housing 1324. In some embodiments, the distalmost surface 1327 of the insert 1326 is parallel and/or coplanar with the distalmost end surface of the outer housing 1324. In some embodiments, the insert 1326 may include a plurality of bores 1328 extending through the insert 1326. In some embodiments, the plurality of bores 1328 may be oriented and/or may extend generally longitudinally through the insert 1326. In at least some embodiments, the plurality of bores 1328 may open distally. Some suitable, but non-limiting, examples of materials for the end cap assembly 1322, the outer housing 1324, and/or the insert 1326 are discussed below.

In some embodiments, the insert 1326 may include a plurality of insert members 1330 (e.g., FIG. 9) and/or an insert member retainer 1332. In some embodiments, the insert member retainer 1332 may include and/or define the distalmost surface 1327 of the insert 1326. In some embodiments, the insert member retainer 1332 may be disposed distally of the plurality of insert members 1330. The insert 1326 may be coaxially received within the outer housing 1324. In some embodiments, the insert 1326 may be fixedly attached to the outer housing 1324, such as by adhesive bonding, mechanical attachment, various forms of welding, or other means. The distalmost surface 1327 may be substantially flat and/or planar. The distalmost surface 1327 of the insert 1326 may be configured to abut and/or contact a proximal surface of the proximal hub 38. In at least some embodiments, the end cap assembly 1322, the outer housing 1324, the insert 1326, and/or the plurality of insert members 1330 may be devoid of any structure configured to engage and/or contact a side surface of the proximal hub 38.

As seen in FIG. 9, each of the plurality of insert members 1330 may include at least a portion of one or more of the plurality of bores 1328 extending through the insert 1326. In some embodiments, each of the plurality of bores 1328 may have an ovoid cross-sectional shape. In the example of FIGS. 8-9, each of the plurality of bores 1328 may be configured to receive one or more of the plurality of wires 130 therein. For example, each of the plurality of bores 1328 may be sized, shaped, and/or configured to receive two of the plurality of wires 130 therein. In some embodiments, the insert member retainer 1332 may be configured to cross over and/or separate a distal opening of each bore 1328 into two apertures, wherein each aperture is configured to receive one of the plurality of wires 130 extending therethrough. When the plurality of insert members 1330 is joined together to collectively form the insert 1326, the plurality of insert member 1330 may join together along and/or at the central longitudinal axis of the insert 1326, which may be coaxial with the central longitudinal axis of the outer housing 1324 in at least some embodiments. In some embodiments, the plurality of insert members 1330 may be fixedly attached together (e.g., adhesively bonded, welded, etc.) when assembled to form the insert 1326. However, fixed attachment between adjacent insert members 1330 is not strictly necessary in all cases.

Figure 10:
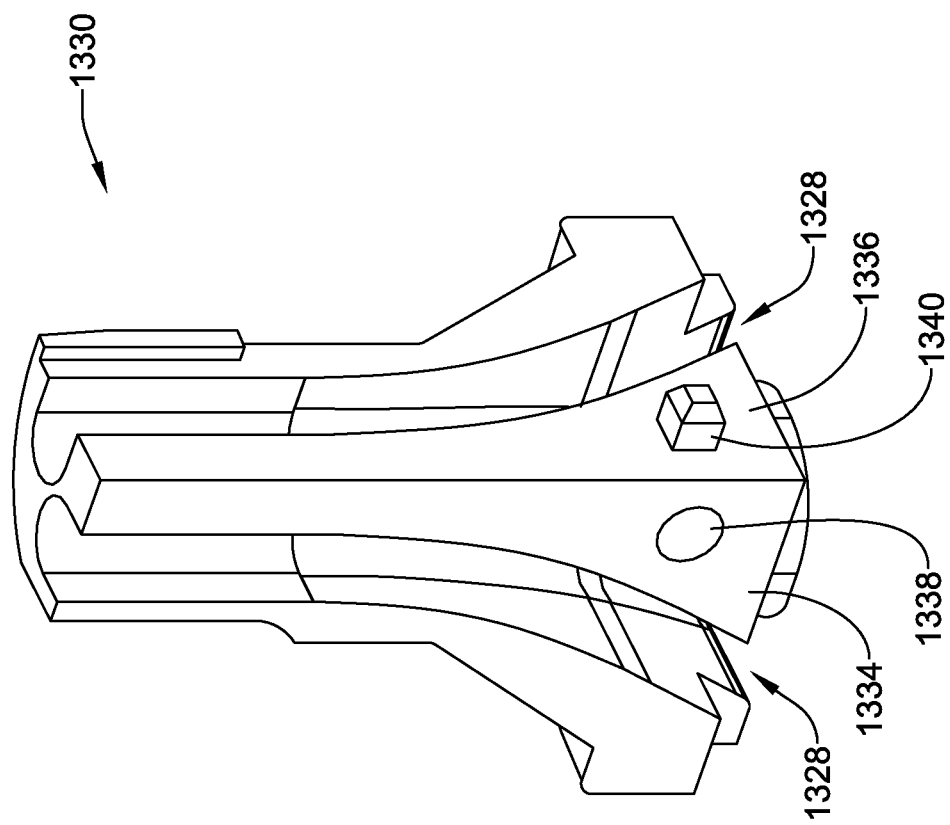
FIG. 10 illustrates aspects of an example insert member of the system of FIGS. 8-9.

FIG. 10 illustrates one of the plurality of insert members 1330 in detail. In some embodiments, the plurality of bores 1328 may be oriented and/or may extend generally longitudinally through the insert 1326 and/or the plurality of insert members 1330. In some embodiments, some and/or each of the plurality of bores 1328 may curve radially outwardly in a distal direction relative to the central longitudinal axis of the insert 1326. The plurality of wires 130 (not shown) may extend through the insert 1326, the plurality of insert members 1330, and/or the plurality of bores 1328. A proximal portion of the plurality of wires 130 may extend proximally from the insert 1326 into the first elongate shaft 104, where the proximal portion of the plurality of wires 130 may be fixedly attached and/or joined to a distal end of the second elongate shaft 116.

Each of the plurality of insert members 1330 may include a first lateral face 1334 and a second lateral face 1336. In some embodiments, the first lateral face 1334 and the second lateral face 1336 may be oriented substantially perpendicular to each other. Other configurations are also possible. The first lateral face 1334 may include a recess 1338 extending into the insert member 1330 and the second lateral face 1336 may include a projection 1340 extending outward therefrom. When the plurality of insert members 1330 are assembled together, the projection 1340 may be received within the recess 1338. For example, the projection 1340 of a first insert member 1330 may be received within the recess 1338 of a second insert member 1330, the projection 1340 of the second insert member 1330 may be received within the recess 1338 of a third insert member 1330, the projection 1340 of the third insert member 1330 may be received within the recess 1338 of a fourth insert member 1330, and the projection 1340 of the fourth insert member 1330 may be received within the recess 1338 of the first insert member 1330. In at least some embodiments, each of the plurality of insert members 1330 may include a distal recess extending proximally from a distally facing surface of the insert member 1330 and configured to receive a portion of the insert member retainer 1332. In some embodiments, the distally facing surface of the insert member 1330 may be substantially parallel to and/or coplanar with the distalmost surface 1327 of the insert member retainer 1332 when the end cap assembly 1322 is fully assembled. As may be seen and/or determined from FIG. 10, each of the plurality of insert members 1330 may include approximately one half of each of the plurality of bores 1328 that extends through it. Accordingly, two adjacent insert members 1330 form each complete bore of the plurality of bores 1328 after being assembled together.

Figure 11:
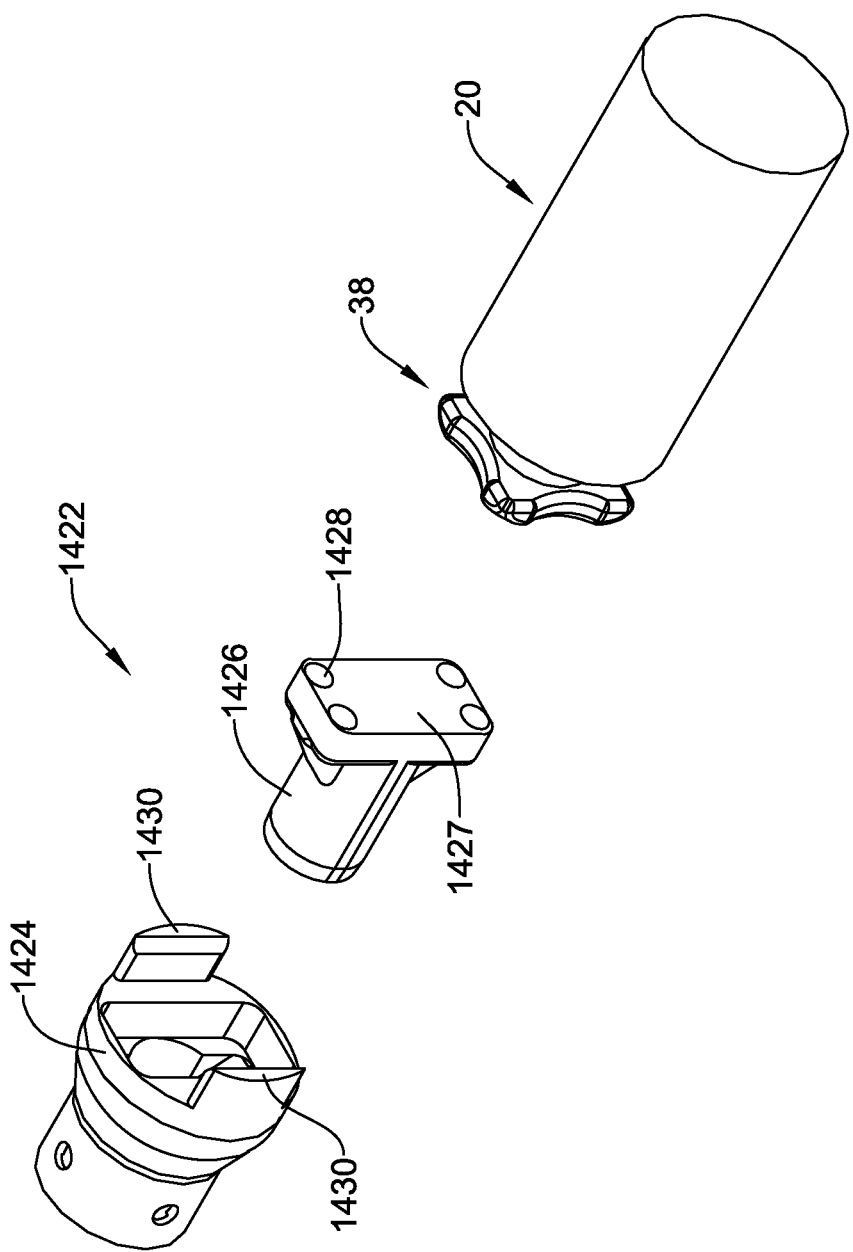
FIG. 11 illustrates aspects of an alternative configuration of the system of FIGS. 3 and 5.

FIG. 11 illustrates aspects of another alternative configuration of the end cap assembly 122. In some embodiments, the system 100 may include an end cap assembly 1422, which may be similar to the end cap assembly 122 in many ways, except as expressly described herein. The end cap assembly 1422 may be disposed at the distal end of the first elongate shaft 104 (not shown). In some embodiments, the end cap assembly 1422 may include an outer housing 1424 fixedly attached to the distal end of the first elongate shaft 104 and an insert 1426 secured within the outer housing 1424. In some embodiments, a distalmost surface 1427 of the insert 1426 is flush with a distalmost end surface of the outer housing 1424. In some embodiments, the distalmost surface 1427 of the insert 1426 is parallel and/or coplanar with the distalmost end surface of the outer housing 1424. In some embodiments, the insert 1426 may include a plurality of bores 1428 extending through the insert 1426. In some embodiments, the plurality of bores 1428 may be oriented and/or may extend generally longitudinally through the insert 1426. In at least some embodiments, the plurality of bores 1428 may open distally. In some embodiments, the outer housing 1424 may include a pair of distally extending extensions 1430. The pair of distally extending extensions 1430 may be configured to engage and/or abut one or more side surfaces of the proximal hub 38 to facilitate transfer of rotational motion from the first elongate shaft 104 to the proximal hub 38. Some suitable, but non-limiting, examples of materials for the end cap assembly 1422, the outer housing 1424, and/or the insert 1426 are discussed below.

FIGS. 12-20 depict an example use (e.g., implantation and retrieval) of the system 100 and the leadless cardiac pacing device 20 within the heart 10. Although the depicted method includes obtaining access to the patient's heart 10 through the inferior vena cava, access to the heart 10 may also or alternatively be obtained through the superior vena cava and/or other approaches. The view of the heart 10 in FIGS. 12-20 is similar to the view depicted in FIG. 1. The broken lines depicted in FIGS. 12-20 depict features that may be covered by one or more other features and that would not ordinarily be viewable from the view depicted. The features in broken lines are shown to assist in describing the disclosed concepts. Further, the features within the coronary sinus 15 are depicted in solid lines for clarity purposes although such features would not ordinarily be viewable from the view depicted.

Figure 12:
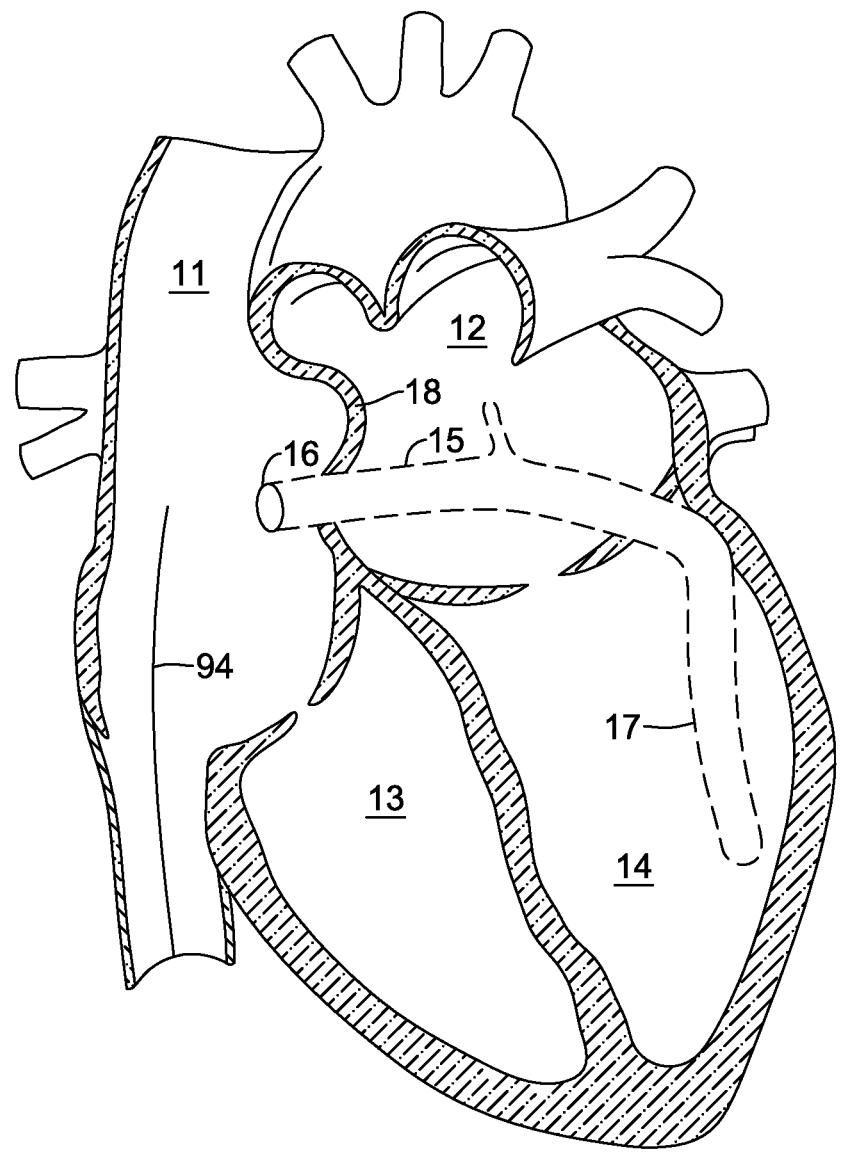
FIGS. 12-20 are a series of schematic diagrams that show delivery and retrieval of a leadless cardiac pacing device into and from a patient's heart.

In some embodiments, implanting the leadless cardiac pacing device 20 within the heart 10 may begin by positioning a guide wire within heart 10, such as a first guide wire 94 depicted in FIG. 12. The first guide wire 94 may have a diameter of 0.035 inches (0.889 mm) and/or may have one or more other suitable diameters for gaining access to the heart 10. The first guide wire 94 may gain access to the heart 10 through an opening in the patient's skin extending into an artery or vein (e.g., the femoral vein or other vessel) that has been dilated with an introducer or other device having a dilation feature (e.g., using a catheter 80 and a dilator 86 as depicted in FIG. 13) and advancing the first guide wire 94 to and/or through the inferior vena cava or other body vessel.

In some instances, the first guide wire 94 may have one or more radiopaque markers disposed on and/or adjacent to a distal end of the first guide wire 94. Such radiopaque markers may allow for easier viewing of the first guide wire 94 through one or more medical imaging systems as the first guide wire 94 is maneuvered into position with the heart 10. In some embodiments, the radiopaque markers may be spaced apart from each other by a known distance. In such embodiments, by counting the number of radiopaque markers between two features within the heart 10, a distance may be determined between the two features. In some embodiments, the leadless cardiac pacing device 20 may be manufactured in a variety of sizes, or various portions of the leadless cardiac pacing device 20, such as the body 22 and the distal extension 24, may be manufactured in various sizes and lengths. By determining a distance between different features of the patient's heart 10, for instance between the coronary sinus ostium 16 and the septum 18 in the right atrium 11, as depicted in FIG. 12, an appropriate sized body 22 or distal extension 24 may be selected for the particular patient.

Figure 13:
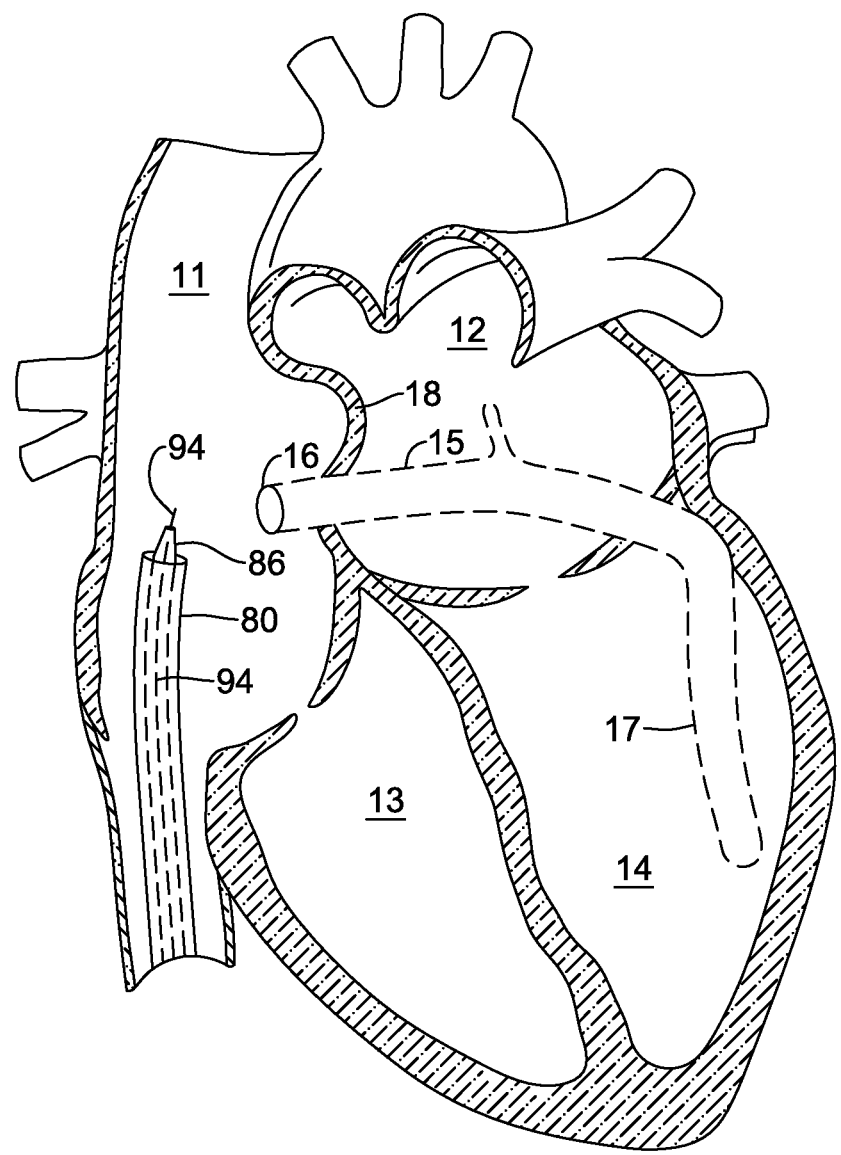

After measuring distances between various features of the heart 10, or in embodiments where such measurements are not needed, the catheter 80 (e.g., an introducer) and the dilator 86 may be maneuvered over the first guide wire 94 into the heart 10, as depicted in FIG. 13. In some cases, the catheter 80 may be steerable and the dilator 86 may be located at or adjacent a distal end (e.g., at or adjacent a distal tip) of the catheter 80. The dilator 86 may be configured to engage the ostium 16 of the coronary sinus 15 and dilate and/or cannulate the coronary sinus 15 such that the catheter 80 and/or the leadless cardiac pacing device 20 may be received therein. Alternatively or in addition, the catheter 80 may have a pre-formed bend at or adjacent a distal end of the catheter 80. In such cases, the dilator 86 may be inserted through the distal end of the catheter 80 to straighten the distal end of the catheter 80 during insertion of the catheter into the heart 10. Then, when the distal end of the catheter 80 is within the heart, such as within the right atrium 11, the dilator 86 may be withdrawn such that the distal end of the catheter 80 bends to face and/or extend into the coronary sinus 15 and/or to direct the first guide wire 94 toward and/or into the coronary sinus 15.

Figure 14:
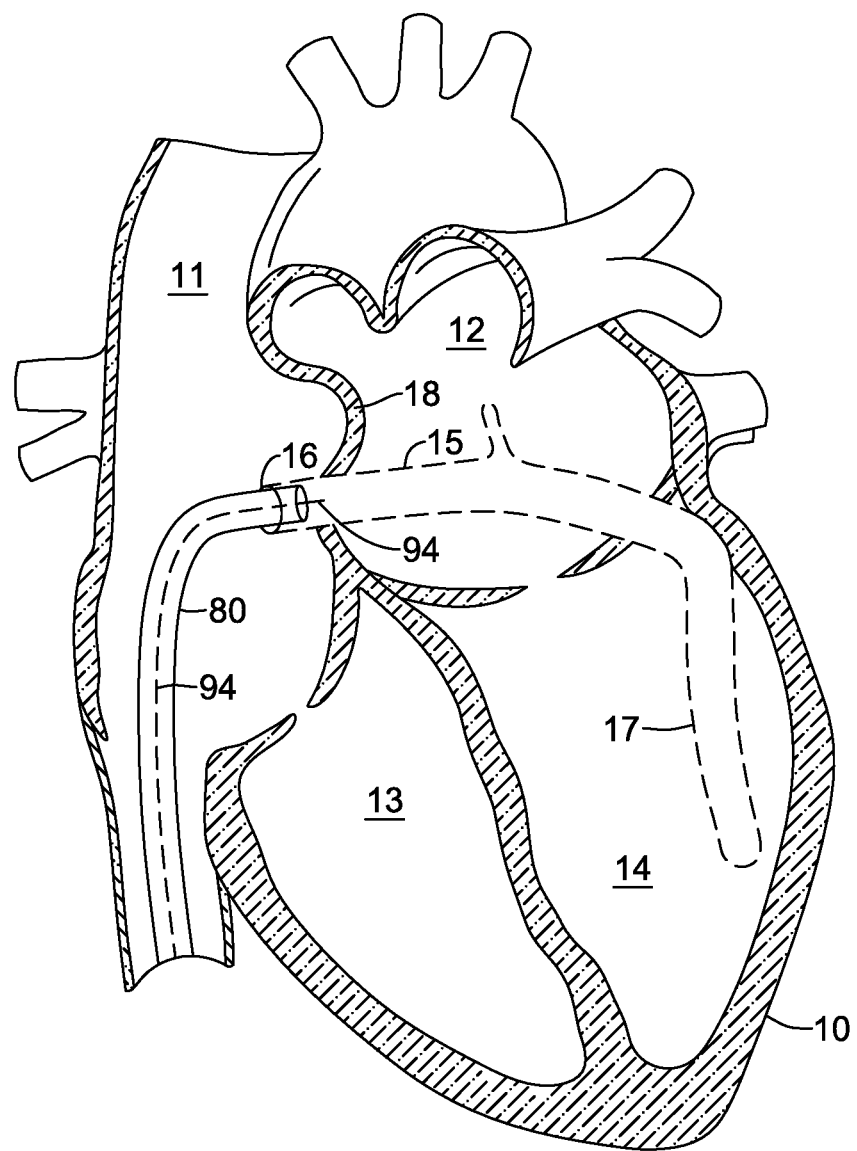

FIG. 14 depicts the catheter 80 and the first guide wire 94 bent and inserted into the coronary sinus 15 after withdrawal of the dilator 86 relative to, through, and/or from the catheter 80. In some cases, after the catheter 80 is bent toward the coronary sinus 15, the first guide wire 94 may be advanced into the coronary sinus 15 and the catheter 80 may be advanced along the first guide wire 94 and into the coronary sinus 15.

The dilator 86 may include a conical tapered tip, such that advancing the catheter 80 and the dilator 86 into the coronary sinus 15 expands the inner diameter of the coronary sinus 15. In another example, the dilator 86 may be rounded or may have a more abrupt taper than a conical taper. Other dilator configurations are contemplated and any configuration suitable for dilating the coronary sinus 15 may be utilized. As such, if the coronary sinus 15 needs to be expanded to receive the leadless cardiac pacing device 20, the distal end or distal tip of the catheter 80 and/or the dilator 86 may be advanced through the ostium 16 of the coronary sinus 15 to dilate the coronary sinus 15 a suitable amount sufficient to receive the leadless cardiac pacing device 20. In addition to or as an alternative to the catheter 80 and/or the dilator 86, one or more other catheters, dilators, or introducers may be used to facilitate dilating, cannulating, and/or otherwise entering the coronary sinus 15.

Figure 15:
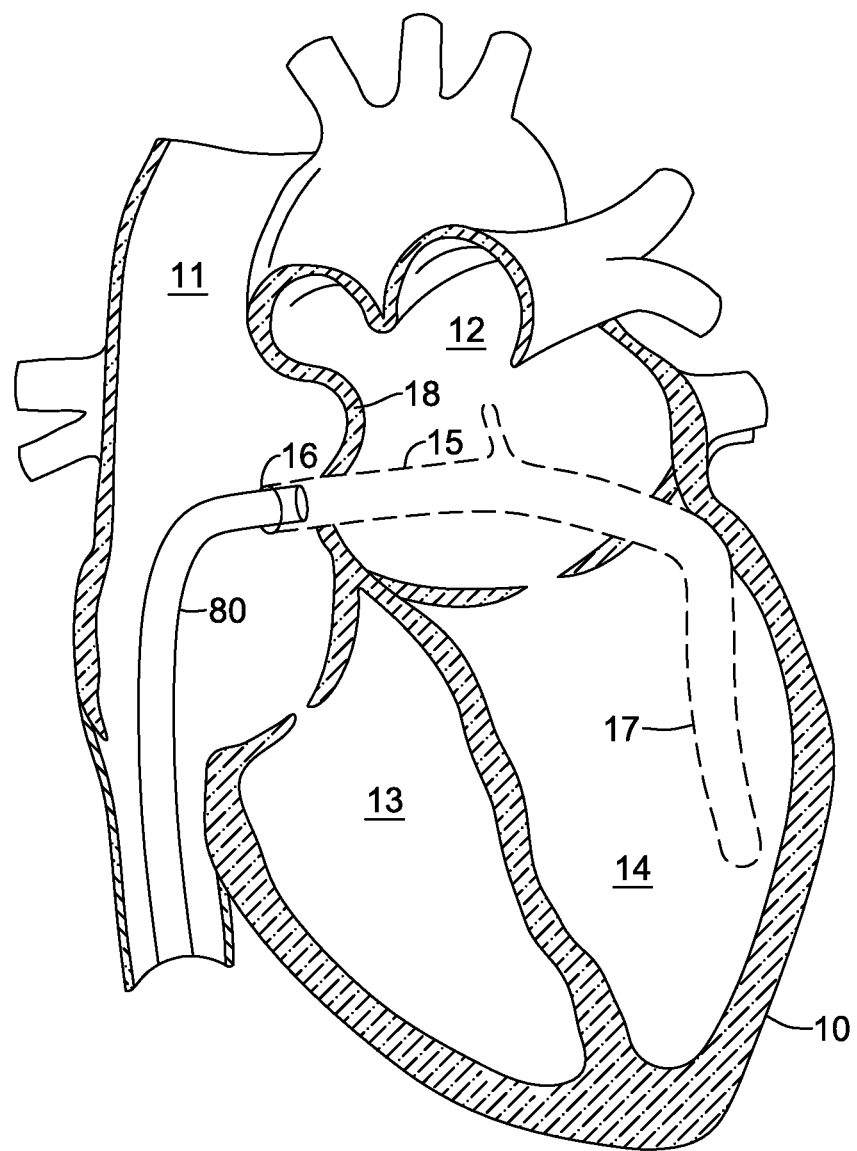
Figure 16:
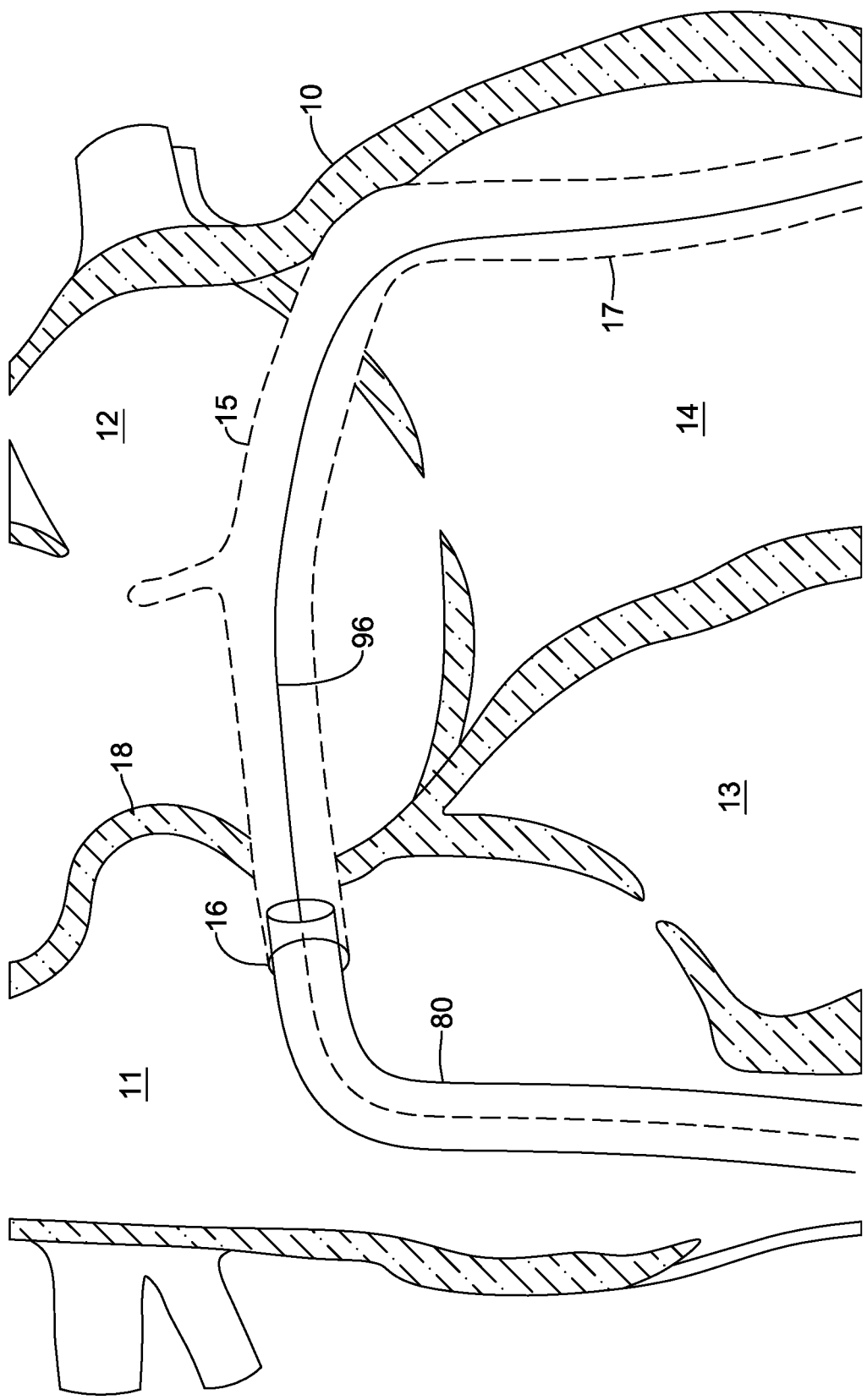

Once the coronary sinus 15 has been cannulated and the catheter 80 inserted therein, the first guide wire 94 may then be removed from the catheter 80, as depicted in FIG. 15. In some instances, a second guide wire 96 may be inserted into and/or through the catheter 80 and maneuvered through coronary sinus 15 and into the great cardiac vein 17 or other vessel extending from the coronary sinus 15, as depicted in FIG. 16. The second guide wire 96 may have a diameter of about 0.014 inches (0.356 mm) and/or other suitable diameter for navigating vessels of and/or extending around the heart 10 (e.g., for navigating the great cardiac vein 17 and/or other vessels extending from or to the great cardiac vein 17). In at least some embodiments, the second guide wire 96 may have a diameter less than the diameter of the first guide wire 94. Alternatively, in some embodiments, the first guide wire 94 may be advanced through the coronary sinus 15 and into the great cardiac vein 17 or other vessel extending from the coronary sinus 15.

Figure 17:
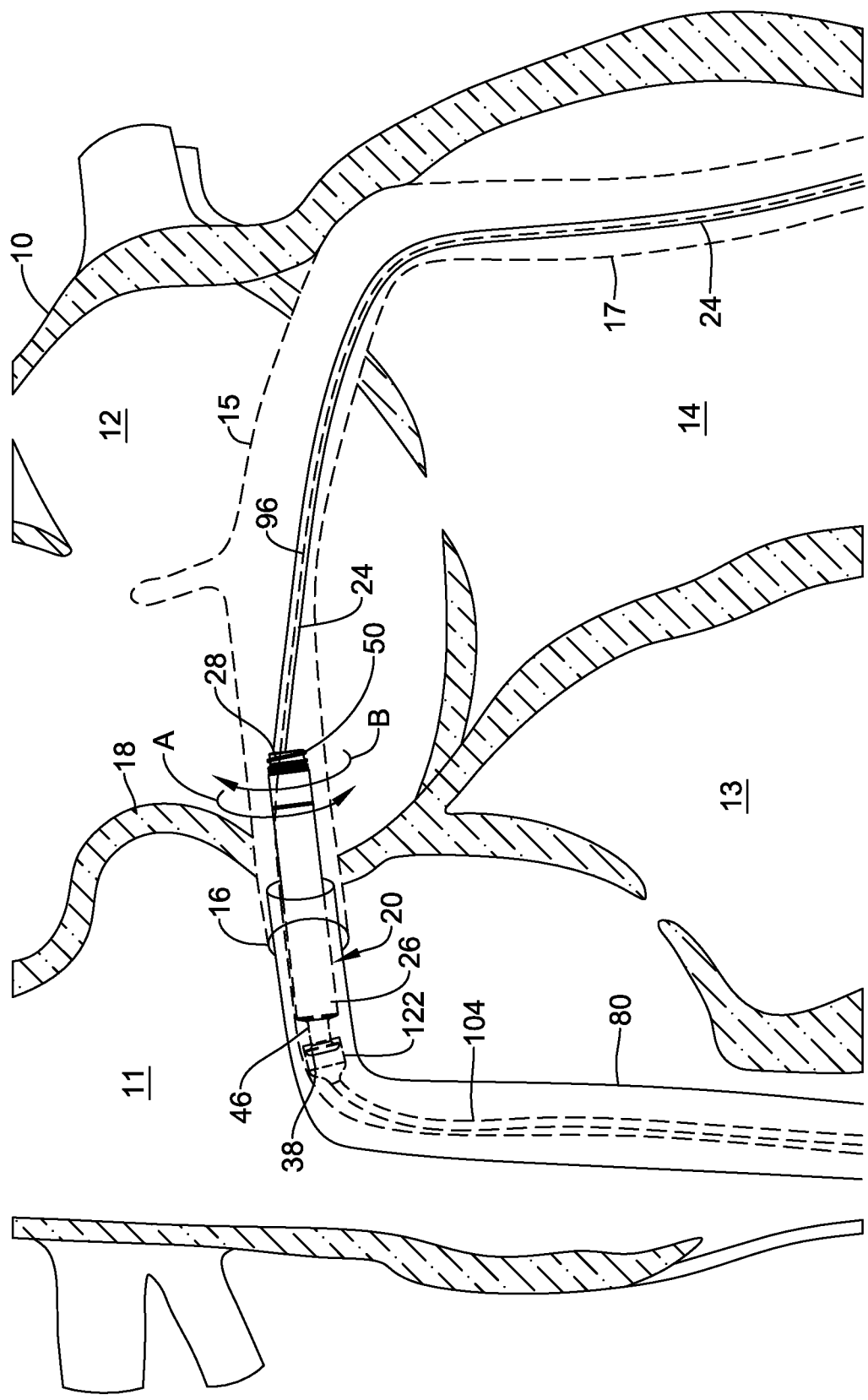

FIG. 17 depicts the catheter 80 and the system 100 including the leadless cardiac pacing device 20 positioned within the coronary sinus 15 with the distal extension 24 tracked over the second guide wire 96 into the great cardiac vein 17 or other cardiac vessel. The second guide wire 96 may exit the guide wire port of the body 22 and extend along an exterior of the body 22. In some embodiments, the proximal end of the body 22 of the leadless cardiac pacing device 20 and the proximal hub 38 may extend proximally out of the coronary sinus 15 into the right atrium 11, with the plurality of wires 130 engaged with the proximal hub 38. The leadless cardiac pacing device 20 may be advanced to this position by pushing the system 100 including the leadless cardiac pacing device 20 through the catheter 80 and over the second guide wire 96 with the plurality of wires 130 engaged with the proximal hub 38. Alternatively, only one of the catheter 80 or the second guide wire 96 may be utilized to position the system 100 and/or the leadless cardiac pacing device 20. Further, it is contemplated that the leadless cardiac pacing device 20 may be positioned with neither of the catheter 80 nor the second guide wire 96.

Once the system 100, the leadless cardiac pacing device 20, and/or the catheter 80 have been position within the coronary sinus 15 adjacent a target location, the system 100, the first elongate shaft 104, and/or the leadless cardiac pacing device 20 may be rotated to position the distal tip 57 of the fixation member 50 at a desired location for puncturing and engaging tissue of the heart 10 and/or the coronary sinus 15. An orientation of the leadless cardiac pacing device 20 within the coronary sinus 15 and/or within the system 100 may be adjusted via interacting with a proximal end of the system 100 and/or may be adjusted in a different suitable manner. In some cases, the orientation of the leadless cardiac pacing device 20 within the coronary sinus 15 and/or within the system 100 may be adjusted by adjusting a position of the leadless cardiac pacing device 20 in a longitudinal direction and/or by rotating the leadless cardiac pacing device 20 in a direction of arrow A and/or arrow B using the system 100 and/or aspects thereof.

In some cases, a rotational and/or longitudinal position of the distal tip 57 may be known or identifiable from one or more radiopaque markers and the known rotational and/or longitudinal position may be utilized for positioning the distal tip 57. In one example, the distal tip 57 may be or may include a radiopaque marker identifiable by one or more imaging systems to facilitate proper alignment of the distal tip 57 of the fixation member 50 with the tissue of the heart 10 and/or the coronary sinus 15. Alternatively or additionally, the fixation member 50 may include one or more other radiopaque features and/or the leadless cardiac pacing device 20 may include one or more radiopaque markers having a known relationship with the distal tip 57 that may be used to position the distal tip 57 at the desired location. In one example, the distal tip 57 may have a first circumferential position, a tail of the fixation member 50 may have a second circumferential position at a predetermined angular orientation from the first circumferential position that may be used to facilitate rotationally aligning the distal tip 57 with target tissue of the heart. Rotation of the leadless cardiac pacing device 20 to rotationally align the distal tip 57 with target tissue of the heart may be performed while the distal tip 57 remains within the lumen of the catheter 80 to prevent unintentional penetration of the distal tip 57 into the tissue, and thereafter the fixation member 50 may be deployed out of the distal end of the catheter 80. Alternatively or additionally, the leadless cardiac pacing device 20 may be rotated in a counter direction of the helical anchor of the fixation member 50 after deploying the distal tip 57 of the fixation member 50 out of the distal end of the catheter 80 to prevent unintentional penetration of the distal tip 57 into the tissue.

Figure 18:
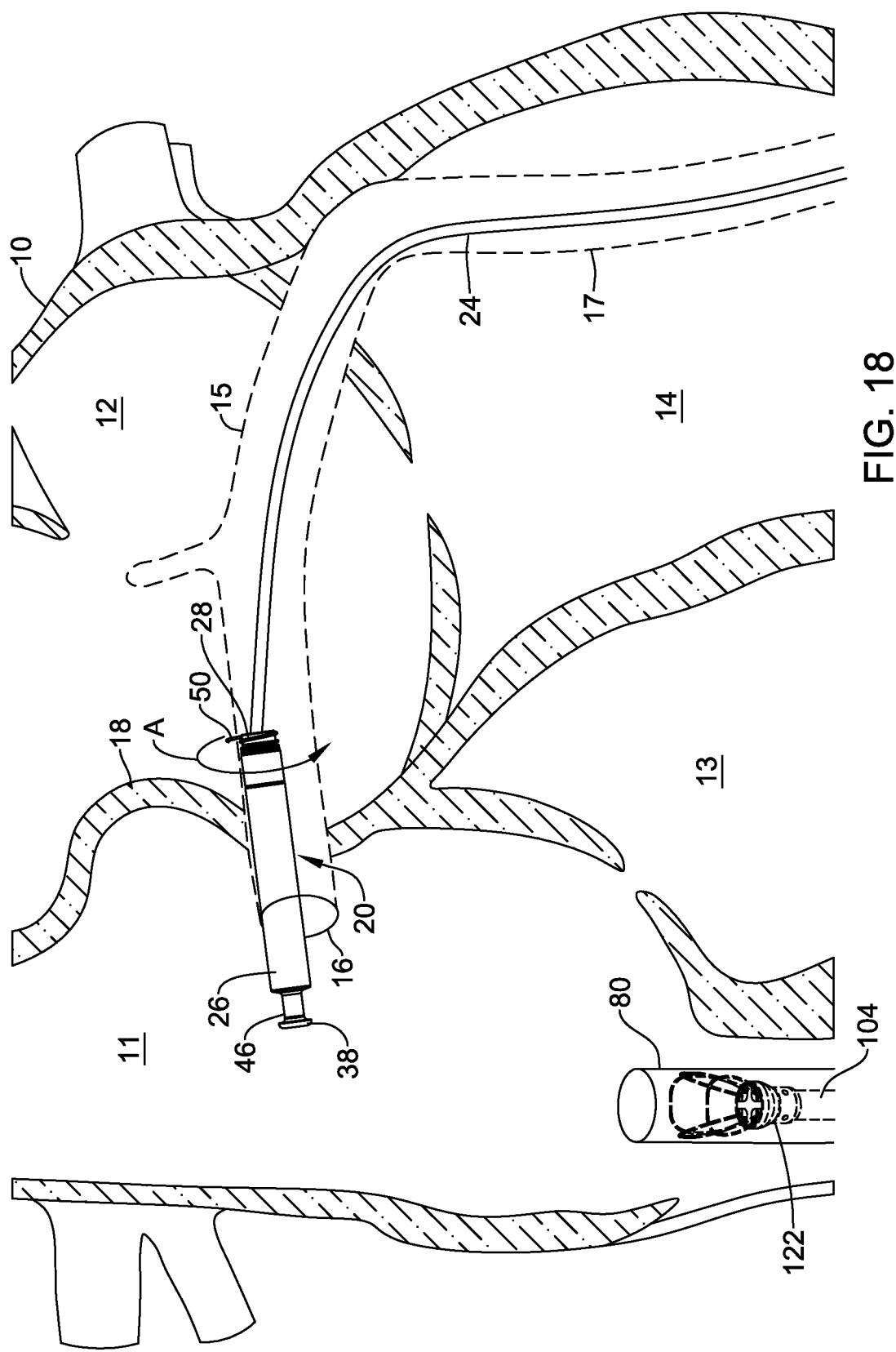

Once the leadless cardiac pacing device 20 is in position, the catheter 80 and the second guide wire 96 may be retracted and the leadless cardiac pacing device 20 may be further rotated using the first elongate shaft 104 (e.g., in the direction of arrow A and/or other suitable direction) such that the distal tip 57 and the fixation member 50 engage tissue of the heart 10 and/or the coronary sinus 15. In some instances, the leadless cardiac pacing device 20 may be oriented such that the distal tip 57 initially penetrates into the left atrial muscle and/or through a wall of the coronary sinus 15. Once the fixation member 50 is engaged with the tissue, the system 100 (less the leadless cardiac pacing device 20) and the catheter 80 may be retracted and, optionally, removed from the heart 10. FIG. 18 depicts an example of how the leadless cardiac pacing device 20 may be positioned after the system 100, the catheter 80, and the second guide wire 96 have been retracted and the fixation member 50 has engaged the tissue of the heart 10. Although the body 22 of the leadless cardiac pacing device 20 is depicted as extending along the right atrium 11 and the left atrium 12 in the coronary sinus 15, the body 22 of the leadless cardiac pacing device 20 may be entirely positioned along the right atrium 11 or entirely along the left atrium 12 within the coronary sinus 15. In some instances the body 22 of the leadless cardiac pacing device 20 may be located along both of the right atrium 11 and the left atrium 12 such that at least part of the first electrode 26 is in contact with tissue of the right atrium 11 and at least part of the second electrode 28 is in contact with tissue of the left atrium 12. In such instances, the leadless cardiac pacing device 20 may be programmed to sense and/or pace one or more of the right atrium 11 and left atrium 12 with the respective electrodes 26, 28 or other electrodes due to the electrodes being bipolar.

Figure 19:
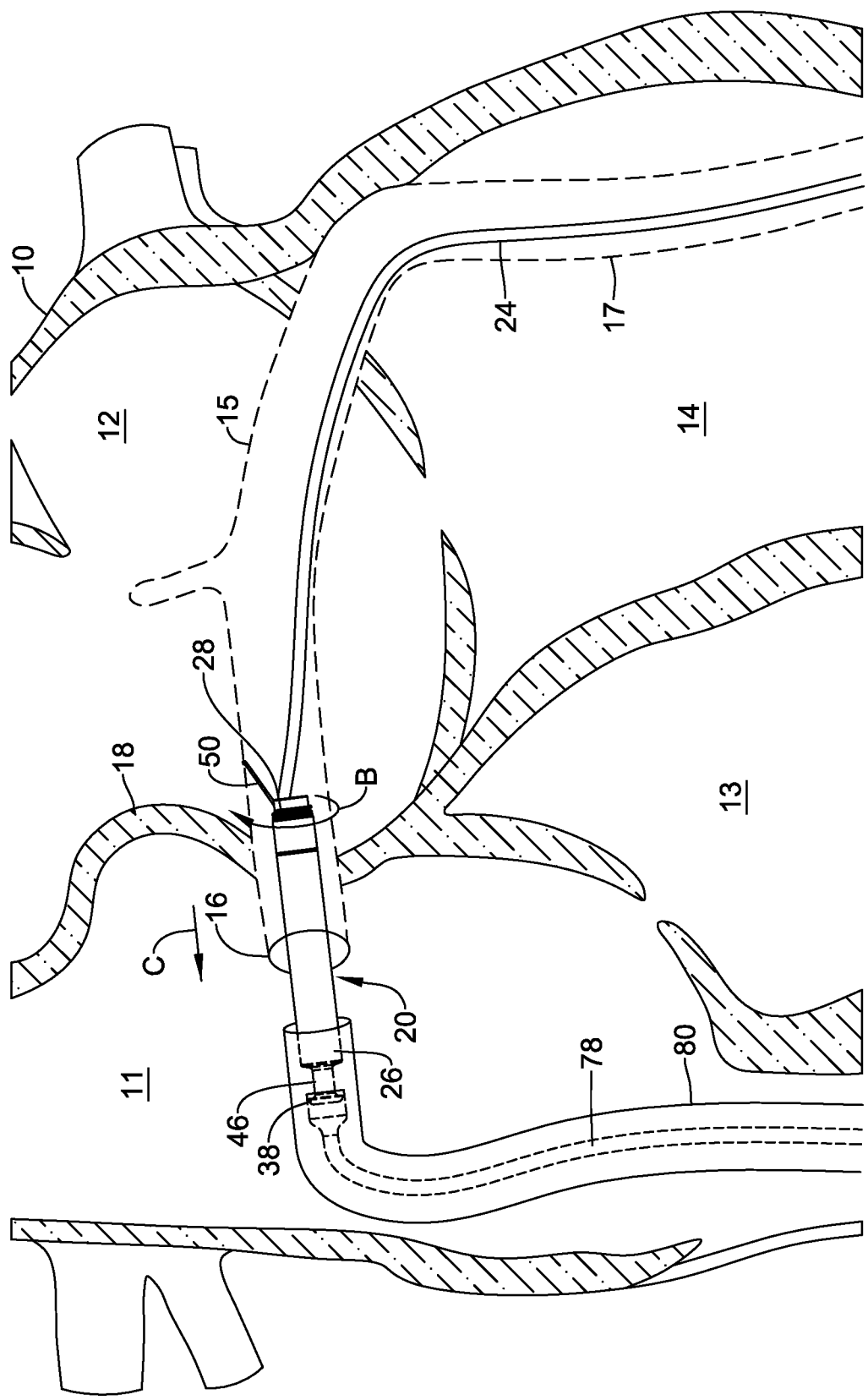

In some cases, the implanted leadless cardiac pacing device 20 may be removed from the coronary sinus 15 and/or the positioning of the implanted leadless cardiac pacing device 20 may be adjusted. FIG. 19 depicts the catheter 80 and a retrieval device 78 (e.g., a implantation and/or retrieval device, which may be or may not be the system 100 or similar to the system 100) inserted into the coronary sinus 15, with the retrieval device 78 (e.g., the end cap assembly 122 and/or the plurality of wires 130 of the system 100) engaging the proximal hub 38 of the leadless cardiac pacing device 20. Once the retrieval device 78 (e.g., the end cap assembly 122 and/or the plurality of wires 130 of the system 100) has engaged the proximal hub 38 of the leadless cardiac pacing device 20, the retrieval device 78 (e.g., the system 100) may apply a force to the leadless cardiac pacing device causing the leadless cardiac pacing device 20 to rotate in a direction of arrow B or other suitable direction. Rotation of the leadless cardiac pacing device 20 may result in the fixation member 50 at least partially withdrawing from engagement with the tissue of the heart 10.

In addition to or as an alternative to rotating the leadless cardiac pacing device 20 in the direction of arrow B, a longitudinal and/or axial force may be applied to the leadless cardiac pacing device 20 in a direction of arrow C (e.g., a longitudinal direction). When the fixation member 50 is still engaged with the tissue of the heart, applying the longitudinal and/or axial force to the leadless cardiac pacing device 20 in the longitudinal direction of arrow C may cause the fixation member 50 to elongate (e.g., straighten and/or elongate in one or more other suitable manners), as shown in FIG. 19 and facilitate removing the fixation member 50 from tissue of the heart 10. Depending on the material configurations utilized, an axial force in the range of about 0.1-1.0 pound-force (lbf), in the range of about 0.1-0.5 lbf, at least about 0.25 lbf, at least about 0.50 lbf, at least about 0.25 lbf but less than about 1.0 lbf, and/or other suitable force amount may be utilized to elongate the fixation member 50. In some instances, the fixation member 50 may be plastically deformed into a straightened configuration by applying the longitudinal and/or axial force in the direction of arrow C for removal from the tissue of the heart 10.

Figure 20:
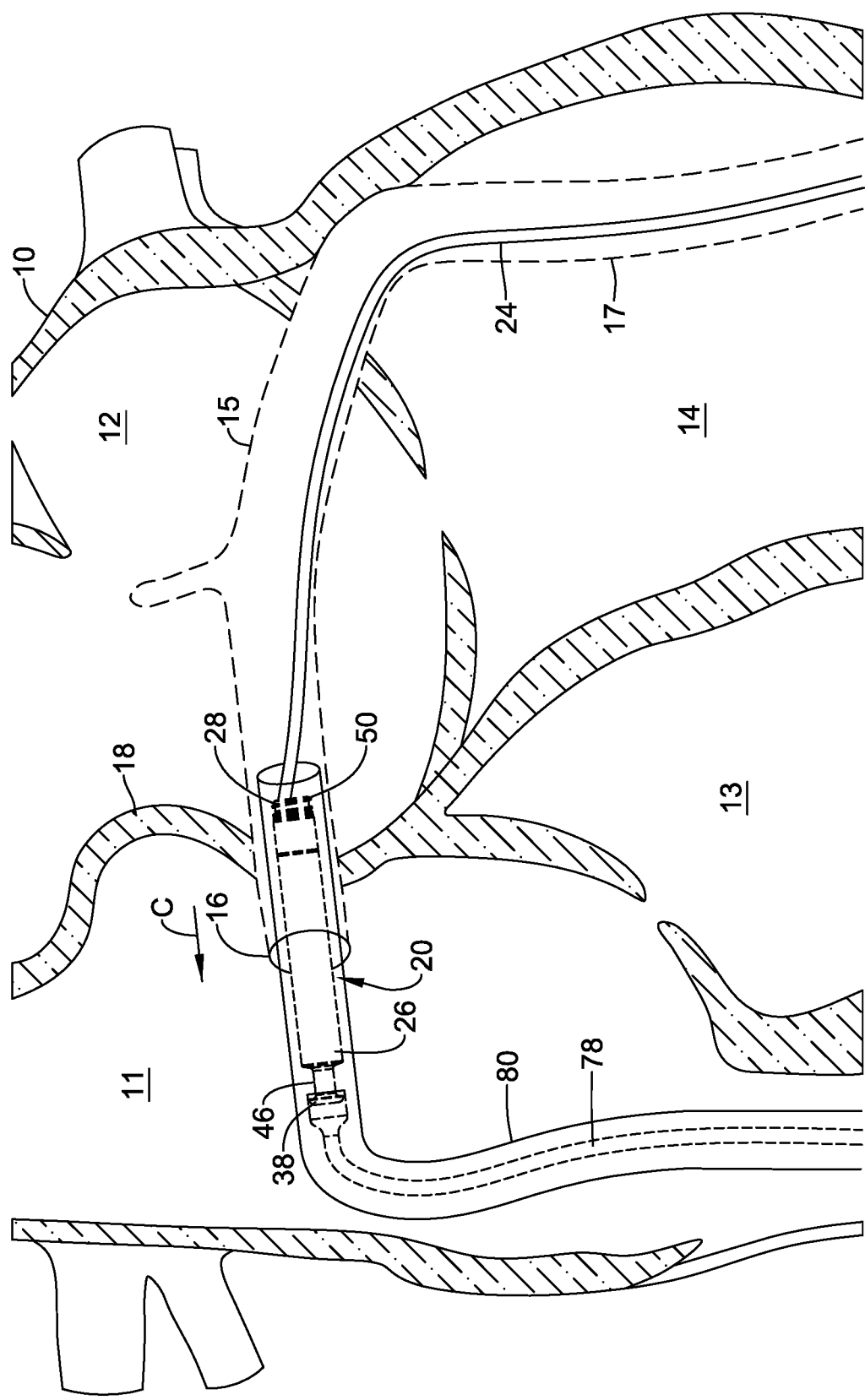

After the fixation member 50 has been completely removed from the tissue of the heart 10 as shown in FIG. 20, the catheter 80 may be advanced over a portion of or an entirety of the leadless cardiac pacing device 20 via relative movement of the retrieval device 78 (e.g., the system 100) and the catheter 80. Once covered by the catheter 80, the leadless cardiac pacing device 20 may be completely withdrawn from the coronary sinus 15 and the patient's heart 10 by applying a further force in the direction C and/or repositioned (e.g., to improve positioning of electrodes of the leadless cardiac pacing device 20 and/or for one or more other suitable reasons) within the coronary sinus 15 and/or the vessels in communication with the coronary sinus 15 by applying a rotational force in direction A (e.g., FIGS. 17-18) to re-engage the fixation member 50 with tissue adjacent the coronary sinus 15.

In some cases, the catheter 80 may be inserted into the vasculature of the patient (e.g., into the coronary sinus 15) and positioned over at least part of the leadless cardiac pacing device 20 and/or the retrieval device 78 (e.g., the system 100) to facilitate withdrawing the leadless cardiac pacing device 20 from the coronary sinus 15. In such cases, the catheter 80 may be positioned at a location covering a proximal end of the leadless cardiac pacing device 20 and the retrieval device 78 (e.g., the system 100) may be advanced through the catheter 80 to the leadless cardiac pacing device 20 at least partially covered by the catheter 80. The positioning of the catheter 80 over the proximal end of the leadless cardiac pacing device 20 may include deflecting a distal end portion of the catheter 80 into the coronary sinus 15 and steering the catheter 80 over the proximal end of the leadless cardiac pacing device 20. The deflection and steering of the catheter 80 may be effected by manipulating one or more control features adjacent a proximal end of the catheter 80 and/or the catheter 80 may have a pre-formed bend configured to bend toward the coronary sinus 15. In some embodiments, the leadless cardiac pacing device 20 may be removed using only the retrieval device 78 (e.g., the system 100) without the presence of the catheter 80.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the first elongate shaft, the second elongate shaft, the end cap assembly, the outer housing, the insert, the plurality of wires, the leadless cardiac pacing device, the handle(s), and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An implantation and/or retrieval device for a leadless cardiac pacing device, comprising:
a first elongate shaft including a lumen;
a second elongate shaft slidably disposed within the lumen of the first elongate shaft;
an end cap assembly fixedly attached to a distal end of the first elongate shaft; and
a plurality of wires attached to the second elongate shaft and extending distally from the end cap assembly, the plurality of wires being movable relative to the end cap assembly;
wherein the plurality of wires is configured to engage a proximal hub of the leadless cardiac pacing device;
wherein the plurality of wires forms a plurality of wire loops extending distally from the end cap assembly;
wherein the end cap assembly includes an insert secured within an outer housing, the outer housing being fixedly attached to the distal end of the first elongate shaft;
wherein the insert includes a plurality of bores extending through the insert, wherein the plurality of bores is configured to receive the plurality of wires;
wherein the insert comprises a plurality of insert members, each insert member including at least a portion of one or more of the plurality of bores extending through the insert member.

2. The implantation and/or retrieval device of claim 1, wherein circumferentially adjacent wire loops of the plurality of wire loops crisscross each other when viewed axially.

3. An implantation and/or retrieval device for a leadless cardiac pacing device, comprising:
a first elongate shaft including a lumen;
a second elongate shaft slidably disposed within the lumen of the first elongate shaft;
an end cap assembly fixedly attached to a distal end of the first elongate shaft; and
a plurality of wires attached to the second elongate shaft and extending distally from the end cap assembly, the plurality of wires being movable relative to the end cap assembly;
wherein the plurality of wires is configured to engage a proximal hub of the leadless cardiac pacing device;
wherein the plurality of wires forms a plurality of wire loops extending distally from the end cap assembly;
wherein the end cap assembly includes an insert secured within an outer housing, the outer housing being fixedly attached to the distal end of the first elongate shaft; and
wherein a distalmost surface of the insert is flush with a distalmost end surface of the outer housing.

4. The implantation and/or retrieval device of claim 3, wherein the insert includes a plurality of bores extending through the insert, wherein the plurality of bores is configured to receive the plurality of wires.

5. The implantation and/or retrieval device of claim 4, wherein the insert is a unitary structure.

6. The implantation and/or retrieval device of claim 4, wherein the insert comprises a plurality of insert members, each insert member including at least a portion of one or more of the plurality of bores extending through the insert member.

7. The implantation and/or retrieval device of claim 4, wherein each of the plurality of bores is configured to receive more than one of the plurality of wires.

8. An implantation and/or retrieval device for a leadless cardiac pacing device, comprising:
a first elongate shaft including a lumen;
a second elongate shaft slidably disposed within the lumen of the first elongate shaft;

an end cap assembly fixedly attached to a distal end of the first elongate shaft; and
a plurality of wires attached to the second elongate shaft and extending distally from the end cap assembly, the plurality of wires being movable relative to the end cap assembly;
wherein the plurality of wires is configured to engage a proximal hub of the leadless cardiac pacing device;
wherein the plurality of wires forms a plurality of wire loops extending distally from the end cap assembly;
wherein the end cap assembly includes an insert secured within an outer housing, the outer housing being fixedly attached to the distal end of the first elongate shaft;
wherein the insert includes a plurality of bores extending through the insert, wherein the plurality of bores is configured to receive the plurality of wires; and
wherein each of the plurality of bores curves radially outwardly in a distal direction.

9. The implantation and/or retrieval device of claim 8, wherein circumferentially adjacent wire loops of the plurality of wire loops crisscross each other when viewed axially.

10. An implantation and/or retrieval device for a leadless cardiac pacing device, comprising:
a first elongate shaft including a lumen;
an end cap assembly fixedly attached to a distal end of the first elongate shaft; and
a plurality of wires extending through the end cap assembly and forming a plurality of wire loops distal of the end cap assembly, the plurality of wires being movable through the end cap assembly between a first position and a second position distal of the first position;
wherein the plurality of wire loops is configured to secure the proximal hub of the leadless cardiac pacing device relative to the end cap assembly in the first position;
wherein the end cap assembly includes an insert secured within an outer housing, the insert including:
a distalmost surface that is flush with a distalmost surface of the outer housing; and
a plurality of bores extending through the insert and opening distally;
wherein the plurality of wire loops is configured to secure the proximal hub of the leadless cardiac pacing device against the distalmost surface of the insert in the first position.

11. The implantation and/or retrieval device of claim 10, wherein circumferentially adjacent wire loops of the plurality of wire loops crisscross each other when viewed axially.

12. The implantation and/or retrieval device of claim 10, wherein the plurality of wires is configured to transfer rotational motion of the first elongate shaft to the proximal hub in the first position.

13. An implantation and/or retrieval device for a leadless cardiac pacing device, comprising:
a first elongate shaft including a lumen;
an end cap assembly fixedly attached to a distal end of the first elongate shaft; and
a plurality of wires extending through the end cap assembly and forming a plurality of wire loops distal of the end cap assembly, the plurality of wires being movable through the end cap assembly between a first position and a second position distal of the first position;
wherein the plurality of wire loops is configured to secure the proximal hub of the leadless cardiac pacing device relative to the end cap assembly in the first position;
wherein the plurality of wire loops includes:
a first wire loop passing through a first pair of the plurality of bores;
a second wire loop passing through a second pair of the plurality of bores; and
a third wire loop passing through a third pair of the plurality of bores.

14. The implantation and/or retrieval device of claim 13, wherein:
one of the second pair of the plurality of bores is disposed circumferentially between the first pair of the plurality of bores; and
one of the third pair of the plurality of bores is disposed circumferentially between the second pair of the plurality of bores.

15. The implantation and/or retrieval device of claim 13, wherein a distal end segment of the first wire loop is parallel to a distal end segment of the third wire loop, and the distal end segment of the first wire loop is perpendicular to a distal end segment of the second wire loop.

16. A system, comprising:
a leadless cardiac pacing device including a body, a proximal hub, and a helical fixation member opposite the proximal hub;
a catheter;
a first elongate shaft slidably disposed within the catheter, the first elongate shaft including a lumen and a proximal handle;
a second elongate shaft slidably disposed within the lumen of the first elongate shaft;
an end cap assembly including an outer housing fixedly attached to a distal end of the first elongate shaft and an insert secured within the outer housing; and
a plurality of wires fixedly attached to the second elongate shaft and extending distally from the end cap assembly to form a plurality of wire loops translatable between a first position and a second position distal of the first position;
wherein the plurality of wire loops is configured to engage the proximal hub of the leadless cardiac pacing device in the first position;
wherein the end cap assembly is devoid of any structure configured to engage a side surface of the proximal hub.

17. The system of claim 16, wherein the plurality of wires is configured to transfer rotational motion of the first elongate shaft to the proximal hub in the first position.

18. The system of claim 16, wherein circumferentially adjacent wire loops of the plurality of wire loops crisscross each other when viewed axially.

19. A system, comprising:
a leadless cardiac pacing device including a body, a proximal hub, and a helical fixation member opposite the proximal hub;
a catheter;
a first elongate shaft slidably disposed within the catheter, the first elongate shaft including a lumen and a proximal handle;
a second elongate shaft slidably disposed within the lumen of the first elongate shaft an end cap assembly including an outer housing fixedly attached to a distal end of the first elongate shaft and an insert secured within the outer housing; and
a plurality of wires fixedly attached to the second elongate shaft and extending distally from the end cap assembly to form a plurality of wire loops translatable between a first position and a second position distal of the first position;

wherein the plurality of wire loops is configured to engage the proximal hub of the leadless cardiac pacing device in the first position;

wherein the leadless cardiac pacing device includes a neck portion extending longitudinally from the body to the proximal hub;

wherein in the first position, the plurality of wire loops includes three or more intersecting distal end segments forming a bounded opening receiving the neck portion therethrough.

20. The system of claim 19, wherein the plurality of wires is configured to transfer rotational motion of the first elongate shaft to the proximal hub in the first position.

* * * * *